United States Patent [19]

Mulvihill et al.

[11] Patent Number: 5,149,533
[45] Date of Patent: Sep. 22, 1992

[54] MODIFIED T-PA WITH KRINGLE-/REPLACED BY ANOTHER KRINGLE

[75] Inventors: Eileen R. Mulvihill, Seattle, Wash.; Shinji Yoshitake, Yatabe, Japan; Yasunori Ikeda, Ushiku, Japan; Suguru Suzuki, Ushiku, Japan; Akira Hashimoto, Ryugasaki, Japan; Teruaki Yuzuriha, Sakura, Japan; Bjorn A. Nexo, Soborg, Denmark

[73] Assignee: ZymoGenetics, Inc., Seattle, Wash.

[21] Appl. No.: 747,452

[22] Filed: Aug. 12, 1991

Related U.S. Application Data

[63] Continuation of Ser. No. 58,217, Jun. 4, 1987, abandoned.

[51] Int. Cl.$^5$ ................ A61K 37/547; C12N 9/64; C12N 15/58; C07H 21/04
[52] U.S. Cl. ................ 424/94.64; 424/94.63; 435/226; 435/240.2; 435/252.3; 435/320.1; 435/217; 435/214; 536/27; 530/324
[58] Field of Search ............ 435/172.3, 320.1, 240.1, 435/252.3, , 240.2, 212, 217, 226, 214; 536/27; 424/94.63, 94.64; 530/324

[56] References Cited

U.S. PATENT DOCUMENTS

4,766,075  8/1988  Goeddel et al. ........... 435/212 X

FOREIGN PATENT DOCUMENTS

| | | |
|---|---|---|
| 61804/86 | 3/1987 | Australia . |
| 41766 | 12/1981 | European Pat. Off. . |
| 143081 | 5/1985 | European Pat. Off. . |
| 0155387 | 9/1985 | European Pat. Off. ......... 435/172.3 |
| 174835 | 3/1986 | European Pat. Off. . |
| 0213794 | 3/1987 | European Pat. Off. ......... 435/172.3 |
| 227462 | 7/1987 | European Pat. Off. . |
| WO 87/03906 | 7/1987 | PCT Int'l Appl. . |
| WO 87/04722 | 8/1987 | PCT Int'l Appl. .................. 75/100 |
| WO 87/05934 | 10/1987 | PCT Int'l Appl. . |
| 2176703 | 1/1987 | United Kingdom . |
| 2179948 | 3/1987 | United Kingdom . |

OTHER PUBLICATIONS

Pennica et al., "Cloning and Expression of Human Tissue-type Plasminogen Activator cDNA in *E. coli*", *Nature* 301:214–221, 1983.

Degan et al., "Characterization of the Complementary Deoxyribonucleic Acid and Gene Coding for Human Prothrombin", *Biochemistry* 22:2087–2097, 1983.

Banyai et al., "Common Evolutionary Origin of the Fibrin-binding Structures of Fibronectin and Tissue-type Plasminogen Activator", *FEBS Lett.* 163:37–41, 1983.

Vali and Patthy, "The Fibrin-binding Site of Human Plasminogen", *J. Biol. Chem.* 259:13690–13694, 1984.

Wang et al., "Site-Specific Mutagenesis of Human Interleukin-2 Gene: Structure-Function Analysis of the Cysteine Residues", *Science* 224:1431–1433, 1984.

van Zonneveld et al., "On the Relation Between Structure and Function of Human Tissue-type Plasminogen Activator", *Throm. Haemostas.* 54:4,1985.

Kagitani et al., "Expression in *E. coli* of Finger-domain Lacking Tissue-type Plasminogen Activator with High Fibrin Affinity", *FEBS Lett.* 189:145–149, 1985.

(List continued on next page.)

*Primary Examiner*—David L. Lacey
*Assistant Examiner*—Marianne Porta Allen
*Attorney, Agent, or Firm*—Seed and Berry

[57] ABSTRACT

Tissue plasminogen activator analogs exhibiting greater specificity for fibrin than native t-PA are disclosed. The analogs include the K1 domain of native t-PA replaced with another kringle domain mediating the binding of the analog to fibrin. The kringle contains six cysteine residues. The t-PA analogs may further include a variety of substitutions and modifications. Pharmaceutical compositions containing one or more of the t-PA analogs along with a physiologically acceptable carrier or diluent are also disclosed.

12 Claims, 30 Drawing Sheets

OTHER PUBLICATIONS van Zonneveld et al., "On the Interaction of the Finger and the Kringle-2 Domain of Tissue-type Plasminogen Activator with Fibrin", *J. Biol. Chem* 261:14214–14218, 1986.

Forsgren et al., "Molecular Cloning and Characterization of a Full-length cDNA Clone for Human Plasminogen", *FEBS Lett.* 213:254–260, 1987.

Verstraete et al., *Blood*, vol. 67, No. 6, pp. 1529–1541, Jun., 1986.

van Zonneveld et al., *Proc. Natl. Acad. Sci.*, vol. 83, pp. 4670–4674, Jul., 1986.

De Marco et al., *J. Biol. Chem*, vol. 257, pp. 12716–12721, 1982.

Suggs et al., *Proc. Natl. Acad Sci.*, vol. 78, pp. 6613–6617, 1981.

Malinowski et al., *Biochemistry*, vol. 23, pp. 4243–4250, 1984.

McMullen et al., *J. Biol. Chem*, vol. 260, pp. 5323–5341, 1985.

Collen, "On the Regulation and Control of Fibrinolysis", *Throm. Haemostas.* 43:77–89, 1980.

Hoylaerts et al., "Kinetics of the Activation of Plasminogen by Human Tissue Plasminogen Activator", *J. Biol. Chem.* 257:2912–2919, 1982.

Edlund et al., "Isolation of cDNA Sequences Coding for a Part of Human Tissue Plasminogen Activator", *Proc. Natl. Acad. Sci. USA* 80:349–352, 1983.

FIG. 1A

```
            10                     30                        45
AAGCTTGGAT CCACC ATG GAT GCA ATG AAG AGA GGG CTC TGC TGT GTG CTG CTG CTG
                  MET Asp Ala MET Lys Arg Gly Leu Cys Cys Val Leu Leu Leu
                  -35                 -30
   60                 75                     90                   105
TGT GGC GCC GTC TTC GTT TCG CCC AGC CAG GAA ATC CAT GCC CGA TTC AGA AGA
Cys Gly Ala Val Phe Val Ser Pro Ser Gln Glu Ile His Ala Arg Phe Arg Arg
        -20                             -10
         120               135                    150               165
GGA GCC AGA TCT TAC CAA GTG ATC TGC AGA GAT GAA AAA ACG CAG ATG ATA TAC
Gly Ala Arg Ser Tyr Gln Val Ile Cys Arg Asp Glu Lys Thr Gln MET Ile Tyr
            1                                      10
             180                195                   210
CAG CAA CAT CAG TCA TGG CTG CGC CCT GTG CTC AGA AGC AAC CGG GTG GAA TAT
Gln Gln His Gln Ser Trp Leu Arg Pro Val Leu Arg Ser Asn Arg Val Glu Tyr
                20                                  30
         225               240                    255               270
TGC TGG TGC AAC AGT GGC AGG GCA CAG TGC CAC TCA GTG CCT GTC AAA AGT TGC
Cys Trp Cys Asn Ser Gly Arg Ala Gln Cys His Ser Val Pro Val Lys Ser Cys
                    40                                          50
             285               300                    315
AGC GAG CCA AGG TGT TTC AAC GGG GGC ACC TGC CAG CAG GCC CTG TAC TTC TCA
Ser Glu Pro Arg Cys Phe Asn Gly Gly Thr Cys Gln Gln Ala Leu Tyr Phe Ser
                                60
330                345                    360                  375
GAT TTC GTG TGC CAG TGC CCC GAA GGA TTT GCT GGG AAG TGC TGT GAA ATA GAT
Asp Phe Val Cys Gln Cys Pro Glu Gly Phe Ala Gly Lys Cys Cys Glu Ile Asp
 70                                          80
         390               405                    420               435
ACC AGG GCC ACG TGC TAC GAG GAC CAG GGC ATC AGC TAC AGG GGC ACG TGG AGC
Thr Arg Ala Thr Cys Tyr Glu Asp Gln Gly Ile Ser Tyr Arg Gly Thr Trp Ser
        90                                          100
             450                465                   480
ACA GCG GAG AGT GGC GCC GAG TGC ACC AAC TGG AAC AGC AGC GCG TTG GCC CAG
Thr Ala Glu Ser Gly Ala Glu Cys Thr Asn Trp Asn Ser Ser Ala Leu Ala Gln
                110                                      120
         495               510                    525               540
AAG CCC TAC AGC GGG CGG AGG CCA GAC GCC ATC AGG CTG GGC CTG GGA AAC CAC
Lys Pro Tyr Ser Gly Arg Arg Pro Asp Ala Ile Arg Leu Gly Leu Gly Asn His
                    130                                         140
             555               570                    585
AAC TAC TGC AGA AAC CCA GAT CGA GAC TCA AAG CCC TGG TGC TAC GTC TTT AAG
Asn Tyr Cys Arg Asn Pro Asp Arg Asp Ser Lys Pro Trp Cys Tyr Val Phe Lys
                                150
600                615                    630                  645
GCG GGG AAG TAC AGC TCA GAG TTC TGC AGC ACC CCT GCC TGT CT GAG GGA AAC
Ala Gly Lys Tyr Ser Ser Glu Phe Cys Ser Thr Pro Ala Cys Ser Glu Gly Asn
160                                          170
         660               675                    690               705
AGT GAC TGC TAC TTT GGG AAT GGG TCA GCC TAC CGT GGC ACG CAC AGC CTC ACC
Ser Asp Cys Tyr Phe Gly Asn Gly Ser Ala Tyr Arg Gly Thr His Ser Leu Thr
                180                                      190
```

FIG. 1B

```
                    720                      735                       750
GAG TCG GGT GCC TCC TGC CTC CCG TGG AAT TCC ATG ATC CTG ATA GGC AAG GTT
Glu Ser Gly Ala Ser Cys Leu Pro Trp Asn Ser MET Ile Leu Ile Gly Lys Val
                    200                                              210
        765                      780                     795                      810
TAC ACA GCA CAG AAC CCC AGT GCC CAG GCA CTG GGC CTG GGC AAA CAT AAT TAC
Tyr Thr Ala Gln Asn Pro Ser Ala Gln Ala Leu Gly Leu Gly Lys His Asn Tyr
                                220                                              230
                825                      840                     855
TGC CGG AAT CCT GAT GGG GAT GCC AAG CCC TGG TGC CAC GTG CTG AAG AAC CGC
Cys Arg Asn Pro Asp Gly Asp Ala Lys Pro Trp Cys His Val Leu Lys Asn Arg
                                        240
870                      885                     900                     915
AGG CTG ACG TGG GAG TAC TGT GAT GTG CCC TCC TGC TCC ACC TGC GGC CTG AGA
Arg Leu Thr Trp Glu Tyr Cys Asp Val Pro Ser Cys Ser Thr Cys Gly Leu Arg
250                                              260
        930                      945                     960                      975
CAG TAC AGC CAG CCT CAG TTT CGC ATC AAA GGA GGG CTC TTC GCC GAC ATC GCC
Gln Tyr Ser Gln Pro Gln Phe Arg Ile Lys Gly Gly Leu Phe Ala Asp Ile Ala
                270                                              280
                990                      1005                    1020
TCC CAC CCC TGG CAG GCT GCC ATC TTT GCC AAG CAC AGG AGG TCG CCC GGA GAG
Ser His Pro Trp Gln Ala Ala Ile Phe Ala Lys His Arg Arg Ser Pro Gly Glu
                                290                                              300
        1035                     1050                    1065                     1080
CGG TTC CTG TGC GGC GGC ATA CTC ATC AGC TCC TGC TGG ATT CTC TCT GCC GCC
Arg Phe Leu Cys Gly Gly Ile Leu Ile Ser Ser Cys Trp Ile Leu Ser Ala Ala
                                310                                              320
                1095                     1110                    1125
CAC TGC TTC CAG GAG AGG TTT CCG CCC CAC CAC CTG ACG GTG ATC TTG GGC AGA
His Cys Phe Gln Glu Arg Phe Pro Pro His His Leu Thr Val Ile Leu Gly Arg
                                        330
1140                     1155                    1170                    1185
ACA TAC CGG GTG GTC CCT GGC GAG GAG GAG CAG AAA TTT GAA GTC GAA AAA TAC
Thr Tyr Arg Val Val Pro Gly Glu Glu Glu Gln Lys Phe Glu Val Glu Lys Tyr
340                                              350
        1200                     1215                    1230                     1245
ATT GTC CAT AAG GAA TTC GAT GAT GAC ACT TAC GAC AAT GAC ATT GCG CTG CTG
Ile Val His Lys Glu Phe Asp Asp Asp Thr Tyr Asp Asn Asp Ile Ala Leu Leu
                360                                              370
                1260                     1275                    1290
CAG CTG AAA TCG GAT TCG TCC CGC TGT GCC CAG GAG AGC AGC GTG GTC CGC ACT
Gln Leu Lys Ser Asp Ser Ser Arg Cys Ala Gln Glu Ser Ser Val Val Arg Thr
                                380                                              390
        1305                     1320                    1335                     1350
GTG TGC CTT CCC CCG GCG GAC CTG CAG CTG CCG GAC TGG ACG GAG TGT GAG CTC
Val Cys Leu Pro Pro Ala Asp Leu Gln Leu Pro Asp Trp Thr Glu Cys Glu leu
                                400                                              410
                1365                     1380                    1395
TCC GGC TAC GGC AAG CAT GAG GCC TTG TCT CCT TTC TAT TCG GAG CGG CTG AAG
Ser Gly Tyr Gly Lys His Glu Ala Leu Ser Pro Phe Tyr Ser Glu Arg Leu Lys
                                        420
```

FIG. 1C

```
1410                    1425                    1440                    1455
GAG GCT CAT GTC AGA CTG TAC CCA TCC AGC CGC TGC ACA TCA CAA CAT TTA CTT
Glu Ala His Val Arg Leu Tyr Pro Ser Ser Arg Cys Thr Ser Gln His Leu Leu
430                                     440
            1470                    1485                    1500                    1515
AAC AGA ACA GTC ACC GAC AAC ATG CTG TGT GCT GGA GAC ACT CGG AGC GGC GGG
Asn Arg Thr Val Thr Asp Asn MET Leu Cys Ala Gly Asp Thr Arg Ser Gly Gly
            450                                     460
                    1530                    1545                    1560
CCC CAG GCA AAC TTG CAC GAC GCC TGC CAG GGC GAT TCG GGA GGC CCC CTG GTG
Pro Gln Ala Asn Leu His Asp Ala Cys Gln Gly Asp Ser Gly Gly Pro Leu Val
                    470                                     480
    1575                    1590                    1605                    1620
TGT CTG AAC GAT GGC CGC ATG ACT TTG GTG GGC ATC ATC AGC TGG GGC CTG GGC
Cys Leu Asn Asp Gly Arg MET Thr Leu Val Gly Ile Ile Ser Trp Gly Leu Gly
                            490                                     500
            1635                    1650                    1665
TGT GGA CAG AAG GAT GTC CCG GGT GTG TAC ACC AAG GTT ACC AAC TAC CTA GAC
Cys Gly Gln Lys Asp Val Pro Gly Val Tyr Thr Lys Val Thr Asn Tyr Leu Asp
                                    510
1680                    1695                    1714        1724        1734
TGG ATT CGT GAC AAC ATG CGA CCG TGA CCAGGAACAC CCGACTCCTC AAAAGCAAAT GAGA
Trp Ile Arg Asp Asn MET Arg Pro
520                             527
```

```
                                Cys Lys Thr Gly Asp Gly Lys Asn Tyr Arg Gly Thr Met Ser
                                TGC AAG ACC GGT GAT GGT AAA AAC TAC CGA GGT ACC ATG TCC

Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG

Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT

Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC

Asp Ile Leu Glu Cys
GAT ATC CTG GAA TGC
```

FIG. 3

```
        -35                    -30                                                  -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                              -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                         20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                         40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                         60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                         80
Leu Tyr Phe Ser Asp Phe Val Cys Gln Cys Pro Glu Gly Phe Ala Gly Lys Cys Cys Glu
CTG TAC TTC TCA GAT TTC GTG TGC CAG TGC CCC GAA GGA TTT GCT GGG AAG TGC TGT GAA 90                                        100
Ile Asp Thr Arg Ala Thr Cys Lys Thr Gly Asp Gly Lys Asn Tyr Arg Gly Thr Met Ser
ATA GAT ACG CGT GCC ACG TGC AAG ACC GGT GAT GGT AAA AAC TAC CGA GGT ACC ATG TCC 110                                       120
Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG 130                                       140
Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT 150                                       160
Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC 170                                       180
Asp Ile Leu Glu Cys Ser Glu Gly Asn Ser Asp Cys Tyr Phe Gly Asn Gly Ser Ala Tyr
GAT ATC CTG GAA TGC TCT GAG GGA AAC AGT GAC TGC TAC TTT GGG AAT GGG TCA GCC TAC 190                                       200
Arg Gly Thr His Ser Leu Thr Glu Ser Gly Ala Ser Cys Leu Pro Trp Asn Ser Met Ile
CGT GGC ACG CAC AGC CTC ACC GAG TCG GGT GCC TCC TGC CTC CCG TGG AAT TCC ATG ATC 210                                       220
Leu Ile Gly Lys Val Tyr Thr Ala Gln Asn Pro Ser Ala Gln Ala Leu Gly Leu Gly Lys
CTG ATA GGC AAG GTT TAC ACA GCA CAG AAC CCC AGT GCC CAG GCA CTC GGC CTG GGC AAA
```

```
                230                                           240
His Asn Tyr Cys Arg Asn Pro Asp Gly Asp Ala Lys Pro Trp Cys His Val Leu Lys Asn
CAT AAT TAC TGC CGG AAT CCT GAT GGG GAT GCC AAG CCC TGG TGC CAC GTG CTG AAG AAC 250                                           260
Arg Arg Leu Thr Trp Glu Tyr Cys Asp Val Pro Ser Cys Ser Thr Cys Gly Leu Arg Gln
CGC AGG CTG ACG TGG GAG TAC TGT GAT GTG CCC TCC TGC TCC ACC TGC GGC CTG AGA CAG 270                                           280
Tyr Ser Gln Pro Gln Phe Arg Ile Lys Gly Gly Leu Phe Ala Asp Ile Ala Ser His Pro
TAC AGC CAG CCT CAG TTT CGC ATC AAA GGA GGG CTC TTC GCC GAC ATC GCC TCC CAC CCC 290                                           300
Trp Gln Ala Ala Ile Phe Ala Lys His Arg Arg Ser Pro Gly Glu Arg Phe Leu Cys Gly
TGG CAG GCT GCC ATC TTT GCC AAG CAC AGG AGG TCG CCC GGA GAG CGG TTC CTG TGC GGG 310                                           320
Gly Ile Leu Ile Ser Ser Cys Trp Ile Leu Ser Ala Ala His Cys Phe Gln Glu Arg Phe
GGC ATA CTC ATC AGC TCC TGC TGG ATT CTC TCT GCC GCC CAC TGC TTC CAG GAG AGG TTT 330                                           340
Pro Pro His His Leu Thr Val Ile Leu Gly Arg Thr Tyr Arg Val Val Pro Gly Glu Glu
CCG CCC CAC CAC CTG ACG GTG ATC TTG GGC AGA ACA TAC CGG GTG GTC CCT GGC GAG GAG 350                                           360
Glu Gln Lys Phe Glu Val Glu Lys Tyr Ile Val His Lys Glu Phe Asp Asp Asp Thr Tyr
GAG CAG AAA TTT GAA GTC GAA AAA TAC ATT GTC CAT AAG GAA TTC GAT GAT GAC ACT TAC 370                                           380
Asp Asn Asp Ile Ala Leu Leu Gln Leu Lys Ser Asp Ser Ser Arg Cys Ala Gln Glu Ser
GAC AAT GAC ATT GCG CTG CTG CAG CTG AAA TCG GAT TCG TCC CGC TGT GCC CAG GAG AGC 390                                           400
Ser Val Val Arg Thr Val Cys Leu Pro Pro Ala Asp Leu Gln Leu Pro Asp Trp Thr Glu
AGC GTG GTC CGC ACT GTG TGC CTT CCC CCG GCG GAC CTG CAG CTG CCG GAC TGG ACG GAG 410                                           420
Cys Glu Leu Ser Gly Tyr Gly Lys His Glu Ala Leu Ser Pro Phe Tyr Ser Glu Arg Leu
TGT GAG CTC TCC GGC TAC GGC AAG CAT GAG GCC TTG TCT CCT TTC TAT TCG GAG CGG CTG 430                                           440
Lys Glu Ala His Val Arg Leu Tyr Pro Ser Ser Arg Cys Thr Ser Gln His Leu Leu Asn
AAG GAG GCT CAT GTC AGA CTG TAC CCA TCC AGC CGC TGC ACA TCA CAA CAT TTA CTT AAC 450                                           460
Arg Thr Val Thr Asp Asn Met Leu Cys Ala Gly Asp Thr Arg Ser Gly Gly Pro Gln Ala
AGA ACA GTC ACC GAC AAC ATG CTG TGT GCT GGA GAC ACT CGG AGC GGC GGG CCC CAG GCA 470                                           480
Asn Leu His Asp Ala Cys Gln Gly Asp Ser Gly Gly Pro Leu Val Cys Leu Asn Asp Gly
AAC TTG CAC GAC GCC TGC CAG GGC GAT TCG GGA GGC CCC CTG GTG TGT CTG AAC GAT GGC
```

```
                    490                                              500
Arg Met Thr Leu Val Gly Ile Ile Ser Trp Gly Leu Gly Cys Gly Gln Lys Asp Val Pro
CGC ATG ACT TTG GTG GGC ATC ATC AGC TGG GGC CTG GGC TGT GGA CAG AAG GAT GTC CCG 510                                              520         524
Gly Val Tyr Thr Lys Val Thr Asn Tyr Leu Asp Trp Ile Arg Asp Asn Met Arg Pro ---
GGT GTG TAC ACC AAG GTT ACC AAC TAC CTA GAC TGG ATT CGT GAC AAC ATG CGA CCG TGA
```

FIG. 9C

```
-35                         -30                                             -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                     -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                      20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                      40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                      60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                      80
Leu Tyr Phe Ser Asp Phe Val Cys Gln Cys Pro Glu Gly Phe Ala Gly Lys Cys Cys Glu
CTG TAC TTC TCA GAT TTC GTG TGC CAG TGC CCC GAA GGA TTT GCT GGG AAG TGC TGT GAA 90                                     100
Ile Asp Thr Arg Ala Thr Cys Lys Thr Gly Asn Gly Lys Asn Tyr Arg Gly Thr Met Ser
ATA GAT ACG CGT GCC ACG TGC AAG ACC GGT AAT GGT AAA AAC TAC CGA GGT ACG ATG TCC 110                                     120
Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG 130                                     140
Phe Ser Pro Ala Thr His Pro Ser Glu Gly Leu Glu Glu Asn Tyr Cys Arg Asn Pro Asp
TTT TCT CCA GCT ACG CAT CCA TCT GAA GGC CTG GAA GAG AAT TAC TGT AGG AAT CCA GAT 150                                     160
Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC 170                                     180
Asp Ile Leu Glu Cys Ser Glu Gly Asn Ser Asp Cys Tyr Phe Gly Asn Gly Ser Ala Tyr
GAT ATC CTG GAA TGC TCT GAG GGA AAC AGT GAC TGC TAC TTT GGG AAT GGG TCA GCC TAC 190                                     200
Arg Gly Thr His Ser Leu Thr Glu Ser Gly Ala Ser Cys Leu Pro Trp Asn Ser Met Ile
CGT GGC ACG CAC AGC CTC ACC GAG TCG GGT GCC TCC TGC CTC CCC TGG AAT TCC ATG ATC 210                                     220
Leu Ile Gly Lys Val Tyr Thr Ala Gln Asn Pro Ser Ala Gln Ala Leu Gly Leu Gly Lys
CTG ATA GGC AAG GTT TAC ACA GCA CAG AAC CCC AGT GCC CAG GCA CTG GGC CTG GGC AAA
```

FIG. 10A

```
                          230                                                      240
His Asn Tyr Cys Arg Asn Pro Asp Gly Asp Ala Lys Pro Trp Cys His Val Leu Lys Asn
CAT AAT TAC TGC CGG AAT CCT GAT GGG GAT GCC AAG CCC TGG TGC CAC GTG CTG AAG AAC 250                                                      260
Arg Arg Leu Thr Trp Glu Tyr Cys Asp Val Pro Ser Cys Ser Thr Cys Gly Leu Arg Gln
CGC AGG CTG ACG TGG GAG TAC TGT GAT GTG CCC TCC TGC TCC ACC TGC GGC CTG AGA CAG 270                                                      280
Tyr Ser Gln Pro Gln Phe Arg Ile Lys Gly Gly Leu Phe Ala Asp Ile Ala Ser His Pro
TAC AGC CAG CCT CAG TTT CGC ATC AAA GGA GGG CTC TTC GCC GAC ATC GCC TCC CAC CCC 290                                                      300
Trp Gln Ala Ala Ile Phe Ala Lys His Arg Arg Ser Pro Gly Glu Arg Phe Leu Cys Gly
TGG CAG GCT GCC ATC TTT GCC AAG CAC AGG AGG TCG CCC GGA GAG CGG TTC CTG TGC GGG 310                                                      320
Gly Ile Leu Ile Ser Ser Cys Trp Ile Leu Ser Ala Ala His Cys Phe Gln Glu Arg Phe
GGC ATA CTC ATC AGC TCC TGC TGG ATT CTC TCT GCC GCC CAC TGC TTC CAG GAG AGG TTT 330                                                      340
Pro Pro His His Leu Thr Val Ile Leu Gly Arg Thr Tyr Arg Val Val Pro Gly Glu Glu
CCG CCC CAC CAC CTG ACG GTG ATC TTG GGC AGA ACA TAC CGG GTG GTC CCT GGC GAG GAG 350                                                      360
Glu Gln Lys Phe Glu Val Glu Lys Tyr Ile Val His Lys Glu Phe Asp Asp Asp Thr Tyr
GAG CAG AAA TTT GAA GTC GAA AAA TAC ATT GTC CAT AAG GAA TTC GAT GAT GAC ACT TAC 370                                                      380
Asp Asn Asp Ile Ala Leu Leu Gln Leu Lys Ser Asp Ser Ser Arg Cys Ala Gln Glu Ser
GAC AAT GAC ATT GCG CTG CTG CAG CTG AAA TCG GAT TCG TCC CGC TGT GCC CAG GAG AGC 390                                                      400
Ser Val Val Arg Thr Val Cys Leu Pro Pro Ala Asp Leu Gln Leu Pro Asp Trp Thr Glu
AGC GTC GTC CGC ACT GTG TGC CTT CCC CCG GCG GAC CTG CAG CTG CCG GAC TGG ACG GAG 410                                                      420
Cys Glu Leu Ser Gly Tyr Gly Lys His Glu Ala Leu Ser Pro Phe Tyr Ser Glu Arg Leu
TGT GAG CTC TCC GGC TAC GGC AAG CAT GAG GCC TTG TCT CCT TTC TAT TCG GAG CGG CTG 430                                                      440
Lys Glu Ala His Val Arg Leu Tyr Pro Ser Ser Arg Cys Thr Ser Gln His Leu Leu Asn
AAG GAG GCT CAT GTC AGA CTG TAC CCA TCC AGC CGC TGC ACA TCA CAA CAT TTA CTT AAC 450                                                      460
Arg Thr Val Thr Asp Asn Met Leu Cys Ala Gly Asp Thr Arg Ser Gly Gly Pro Gln Ala
AGA ACA GTC ACC GAC AAC ATG CTG TGT GCT GGA GAC ACT CGG AGC GGC GGG CCC CAG GCA 470                                                      480
Asn Leu His Asp Ala Cys Gln Gly Asp Ser Gly Gly Pro Leu Val Cys Leu Asn Asp Gly
AAC TTG CAC GAC GCC TGC CAG GGC GAT TCG GGA GGC CCC CTG GTG TGT CTC AAC GAT GGC
```

FIG. 10B

```
            490                                    500
Arg Met Thr Leu Val Gly Ile Ile Ser Trp Gly Leu Gly Cys Gly Gln Lys Asp Val Pro
CGC ATG ACT TTG GTG GGC ATC ATC AGC TGG GGC CTG GGC TGT GGA CAG AAG GAT GTC CCG 510                                    520        524
Gly Val Tyr Thr Lys Val Thr Asn Tyr Leu Asp Trp Ile Arg Asp Asn Met Arg Pro ---
GGT GTG TAC ACC AAG GTT ACC AAC TAC CTA GAC TGG ATT CGT GAC AAC ATG CGA CCG TGA
```

FIG. 10C

```
       -35                    -30                                        -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                    -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                      20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                      40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                      60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                      80
Leu Tyr Phe Ser Asp Phe Val Cys Gln Cys Pro Glu Gly Phe Ala Gly Lys Ser Cys Glu
CTG TAC TTC TCA GAT TTC GTG TGC CAG TGC CCC GAA GGA TTT GCT GGG AAG AGC TGT GAA 90                                      100
Ile Asp Thr Arg Ala Thr Cys Tyr Glu Asp Gln Gly Ile Ser Tyr Arg Gly Thr Trp Ser
ATC GAT ACC AGG GCC ACG TGC TAC GAG GAC CAG GGC ATC AGC TAC AGG GGC ACG TGG AGC 110                                     120
Thr Ala Glu Ser Gly Ala Glu Cys Thr Asn Trp Asn Ser Ser Ala Leu Ala Gln Lys Pro
ACA GCG GAG AGT GGC GCC GAG TGC ACC AAC TGG AAC AGC AGC GCG TTG GCC CAG AAG CCC 130                                     140
Tyr Ser Gly Arg Arg Pro Asp Ala Ile Arg Leu Gly Leu Gly Asn His Asn Tyr Cys Arg
TAC AGC GGG CGG AGG CCA GAC GCC ATC AGG CTG GGC CTG GGG AAC CAC AAC TAC TGC AGA 150                                     160
Asn Pro Asp Arg Asp Ser Lys Pro Trp Cys Tyr Val Phe Lys Ala Gly Lys Tyr Ser Ser
AAC CCA GAT CGA GAC TCA AAG CCC TGG TGC TAC GTC TTT AAG GCG GGG AAG TAC AGC TCA 170                                     180
Glu Phe Cys Ser Thr Pro Ala Cys Ser Glu Gly Asn Ser Asp Cys Tyr Phe Gly Asn Gly
GAG TTC TGC AGC ACC CCT GCC TGC TCT GAG GGA AAC AGT GAC TGC TAC TTT GGG AAT GGG 190                                     200
Ser Ala Tyr Arg Gly Thr His Ser Leu Thr Glu Ser Gly Ala Ser Cys Leu Pro Trp Asn
TCA GCC TAC CGT GGC ACG CAC AGC CTC ACC GAG TCG GGT GCC TCC TGC CTC CCG TGG AAT 210                                     220
Ser Met Ile Leu Ile Gly Lys Val Tyr Thr Ala Gln Asn Pro Ser Ala Gln Ala Leu Gly
TCC ATG ATC CTG ATA GGC AAG GTT TAC ACA GCA CAG AAC CCC AGT GCC CAG GCA CTG GGC
```

FIG. 15A

```
                           230                                        240
Leu Gly Lys His Asn Tyr Cys Arg Asn Pro Asp Gly Asp Ala Lys Pro Trp Cys His Val
CTG GGC AAA CAT AAT TAC TGC CGG AAT CCT GAT GGG GAT GCC AAG CCC TGG TGC CAC GTG 250                                        260
Leu Lys Asn Arg Arg Leu Thr Trp Glu Tyr Cys Asp Val Pro Ser Cys Ser Thr Cys Gly
CTG AAG AAC CGC AGG CTG ACG TGG GAG TAC TGT GAT GTG CCC TCC TGC TCC ACC TGC GGC 270                                        280
Leu Arg Gln Tyr Ser Gln Pro Gln Phe Arg Ile Lys Gly Gly Leu Phe Ala Asp Ile Ala
CTG AGA CAG TAC AGC CAG CCT CAG TTT CGC ATC AAA GGA GGG CTC TTC GCC GAC ATC GCC 290                                        300
Ser His Pro Trp Gln Ala Ala Ile Phe Ala Lys His Arg Arg Ser Pro Gly Glu Arg Phe
TCC CAC CCC TGG CAG GCT GCC ATC TTT GCC AAG CAC AGG AGG TCG CCC GGA GAG CGG TTC 310                                        320
Leu Cys Gly Gly Ile Leu Ile Ser Ser Cys Trp Ile Leu Ser Ala Ala His Cys Phe Gln
CTG TGC GGG GGC ATA CTC ATC AGC TCC TGC TGG ATT CTC TCT GCC GCC CAC TGC TTC CAG 330                                        340
Glu Arg Phe Pro Pro His His Leu Thr Val Ile Leu Gly Arg Thr Tyr Arg Val Val Pro
GAG AGG TTT CCG CCC CAC CAC CTG ACG GTG ATC TTG GGC AGA ACA TAC CGG GTG GTC CCT 350                                        360
Gly Glu Glu Glu Gln Lys Phe Glu Val Glu Lys Tyr Ile Val His Lys Glu Phe Asp Asp
GGC GAG GAG GAG CAG AAA TTT GAA GTC GAA AAA TAC ATT GTC CAT AAG GAA TTC GAT GAT 370                                        380
Asp Thr Tyr Asp Asn Asp Ile Ala Leu Leu Gln Leu Lys Ser Asp Ser Ser Arg Cys Ala
GAC ACT TAC GAC AAT GAC ATT GCG CTG CTG CAG CTG AAA TCG GAT TCG TCC CGC TGT GCC 390                                        400
Gln Glu Ser Ser Val Val Arg Thr Val Cys Leu Pro Pro Ala Asp Leu Gln Leu Pro Asp
CAG GAG AGC AGC GTG GTC CGC ACT GTG TGC CTT CCC CCG GCG GAC CTG CAG CTG CCG GAC 410                                        420
Trp Thr Glu Cys Glu Leu Ser Gly Tyr Gly Lys His Glu Ala Leu Ser Pro Phe Tyr Ser
TGG ACG GAG TGT GAG CTC TCC GGC TAC GGC AAG CAT GAG GCC TTG TCT CCT TTC TAT TCG 430                                        440
Glu Arg Leu Lys Glu Ala His Val Arg Leu Tyr Pro Ser Ser Arg Cys Thr Ser Gln His
GAG CGG CTG AAG GAG GCT CAT GTC AGA CTG TAC CCA TCC AGC CGC TGC ACA TCA CAA CAT 450                                        460
Leu Leu Asn Arg Thr Val Thr Asp Asn Met Leu Cys Ala Gly Asp Thr Arg Ser Gly Gly
TTA CTT AAC AGA ACA GTC ACC GAC AAC ATG CTG TGT GCT GGA GAC ACT CGG AGC GGC GGG 470                                        480
Pro Gln Ala Asn Leu His Asp Ala Cys Gln Gly Asp Ser Gly Gly Pro Leu Val Cys Leu
CCC CAG GCA AAC TTG CAC GAC GCC TGC CAG GGC GAT TCG GGA GGC CCC CTG GTG TGT CTG
```

FIG. 15B

```
                   490                                        500
Asn Asp Gly Arg Met Thr Leu Val Gly Ile Ile Ser Trp Gly Leu Gly Cys Gly Gln Lys
AAC GAT GGC CGC ATG ACT TTG GTG GGC ATC ATC AGC TGG GGC CTG GGC TGT GGA CAG AAG 510                                        520
Asp Val Pro Gly Val Tyr Thr Lys Val Thr Asn Tyr Leu Asp Trp Ile Arg Asp Asn Met
GAT GTC CCG GGT GTG TAC ACC AAG GTT ACC AAC TAC CTA GAC TGG ATT CGT GAC AAC ATG

527
Arg Pro ---
CGA CCG TGA
```

FIG. 15C

```
        -35                    -30                                           -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                       -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                         20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                         40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                         60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                         80
Leu Tyr Phe Ser Asp Phe Val Cys Gln Cys Pro Glu Gly Phe Ala Gly Lys Cys Ser Glu
CTG TAC TTC TCA GAT TTC GTG TGC CAG TGC CCC GAA GGA TTT GCT GGG AAG TGC AGT GAA 90                                        100
Ile Asp Thr Arg Ala Thr Cys Tyr Glu Asp Gln Gly Ile Ser Tyr Arg Gly Thr Trp Ser
ATC GAT ACC AGG GCC ACG TGC TAC GAG GAC CAG GGC ATC AGC TAC AGG GGC ACG TGG AGC 110                                        120
Thr Ala Glu Ser Gly Ala Glu Cys Thr Asn Trp Asn Ser Ser Ala Leu Ala Gln Lys Pro
ACA GCG GAG AGT GGC GCC GAG TGC ACC AAC TGG AAC AGC AGC GCG TTG GCC CAG AAG CCC 130                                        140
Tyr Ser Gly Arg Arg Pro Asp Ala Ile Arg Leu Gly Leu Gly Asn His Asn Tyr Cys Arg
TAC AGC GGG CGG AGG CCA GAC GCC ATC AGG CTG GGC CTG GGG AAC CAC AAC TAC TGC AGA 150                                        160
Asn Pro Asp Arg Asp Ser Lys Pro Trp Cys Tyr Val Phe Lys Ala Gly Lys Tyr Ser Ser
AAC CCA GAT CGA GAC TCA AAG CCC TGG TGC TAC GTC TTT AAG GCG GGG AAG TAC AGC TCA 170                                        180
Glu Phe Cys Ser Thr Pro Ala Cys Ser Glu Gly Asn Ser Asp Cys Tyr Phe Gly Asn Gly
GAG TTC TGC AGC ACC CCT GCC TGC TCT GAG GGA AAC AGT GAC TGC TAC TTT GGG AAT GGG 190                                        200
Ser Ala Tyr Arg Gly Thr His Ser Leu Thr Glu Ser Gly Ala Ser Cys Leu Pro Trp Asn
TCA GCC TAC CGT GGC ACG CAC AGC CTC ACC GAG TCG GGT GCC TCC TGC CTC CCG TGG AAT 210                                        220
Ser Met Ile Leu Ile Gly Lys Val Tyr Thr Ala Gln Asn Pro Ser Ala Gln Ala Leu Gly
TCC ATG ATC CTG ATA GGC AAG GTT TAC ACA GCA CAG AAC CCC AGT GCC CAG GCA CTG GGC
```

FIG. 16A

```
                    230                                          240
Leu Gly Lys His Asn Tyr Cys Arg Asn Pro Asp Gly Asp Ala Lys Pro Trp Cys His Val
CTG GGC AAA CAT AAT TAC TGC CGG AAT CCT GAT GGG GAT GCC AAG CCC TGG TGC CAC GTG 250                                          260
Leu Lys Asn Arg Arg Leu Thr Trp Glu Tyr Cys Asp Val Pro Ser Cys Ser Thr Cys Gly
CTG AAG AAC CGC AGG CTG ACG TGG GAG TAC TGT GAT GTG CCC TCC TGC TCC ACC TGC GGC 270                                          280
Leu Arg Gln Tyr Ser Gln Pro Gln Phe Arg Ile Lys Gly Gly Leu Phe Ala Asp Ile Ala
CTG AGA CAG TAC AGC CAG CCT CAG TTT CGC ATC AAA GGA GGG CTC TTC GCC GAC ATC GCC 290                                          300
Ser His Pro Trp Gln Ala Ala Ile Phe Ala Lys His Arg Arg Ser Pro Gly Glu Arg Phe
TCC CAC CCC TGG CAG GCT GCC ATC TTT GCC AAG CAC AGG AGG TCG CCC GGA GAG CGG TTC 310                                          320
Leu Cys Gly Gly Ile Leu Ile Ser Ser Cys Trp Ile Leu Ser Ala Ala His Cys Phe Gln
CTG TGC GGG GGC ATA CTC ATC AGC TCC TGC TGG ATT CTC TCT GCC GCC CAC TGC TTC CAG 330                                          340
Glu Arg Phe Pro Pro His His Leu Thr Val Ile Leu Gly Arg Thr Tyr Arg Val Val Pro
GAG AGG TTT CCG CCC CAC CAC CTG ACG GTG ATC TTG GGC AGA ACA TAC CGG GTG GTC CCT 350                                          360
Gly Glu Glu Glu Gln Lys Phe Glu Val Glu Lys Tyr Ile Val His Lys Glu Phe Asp Asp
GGC GAG GAG GAG CAG AAA TTT GAA GTC GAA AAA TAC ATT GTC CAT AAG GAA TTC GAT GAT 370                                          380
Asp Thr Tyr Asp Asn Asp Ile Ala Leu Leu Gln Leu Lys Ser Asp Ser Ser Arg Cys Ala
GAC ACT TAC GAC AAT GAC ATT GCG CTG CTG CAG CTG AAA TCG GAT TCG TCC CGC TGT GCC 390                                          400
Gln Glu Ser Ser Val Val Arg Thr Val Cys Leu Pro Pro Ala Asp Leu Gln Leu Pro Asp
CAG GAG AGC AGC GTG GTC CGC ACT GTG TGC CTT CCC CCG GCG GAC CTG CAG CTG CCG GAC 410                                          420
Trp Thr Glu Cys Glu Leu Ser Gly Tyr Gly Lys His Glu Ala Leu Ser Pro Phe Tyr Ser
TGG ACG GAG TGT GAG CTC TCC GGC TAC GGC AAG CAT GAG GCC TTG TCT CCT TTC TAT TCG 430                                          440
Glu Arg Leu Lys Glu Ala His Val Arg Leu Tyr Pro Ser Ser Arg Cys Thr Ser Gln His
GAG CGG CTG AAG GAG GCT CAT GTC AGA CTG TAC CCA TCC AGC CGC TGC ACA TCA CAA CAT 450                                          460
Leu Leu Asn Arg Thr Val Thr Asp Asn Met Leu Cys Ala Gly Asp Thr Arg Ser Gly Gly
TTA CTT AAC AGA ACA GTC ACC GAC AAC ATG CTG TGT GCT GGA GAC ACT CGG AGC GGC GGG 470                                          480
Pro Gln Ala Asn Leu His Asp Ala Cys Gln Gly Asp Ser Gly Gly Pro Leu Val Cys Leu
CCC CAG GCA AAC TTG CAC GAC GCC TGC CAG GGC GAT TCG GGA GGC CCC CTG GTG TGT CTG
```

FIG. 16B

```
                    490                                          500
Asn Asp Gly Arg Met Thr Leu Val Gly Ile Ile Ser Trp Gly Leu Gly Cys Gly Gln Lys
AAC GAT GGC CGC ATG ACT TTG GTG GGC ATC ATC AGC TGG GGC CTG GGC TGT GGA CAG AAG 510                                          520
Asp Val Pro Gly Val Tyr Thr Lys Val Thr Asn Tyr Leu Asp Trp Ile Arg Asp Asn Met
GAT GTC CCG GGT GTG TAC ACC AAG GTT ACC AAC TAC CTA GAC TGG ATT CGT GAC AAC ATG

527
Arg Pro —
CGA CCG TGA
```

FIG. 16C

| | |
|---|---|
| 19A | CRDEKTQMIYQQHQSWLRPVLRSNRVEYCWCNSGRAQC |
| 19B | CFDNGKSYKIGETWERPYEGFMLSCTCLGNGRGEFRC |
| 19C | CHDEKTGSSYKIGEQWERPYLSGNRLECTCLGNGSGRWQC |
| 19D | CFDNGKSYKIGETWERPYEGFMLSCTCLGNGSGRWQC |
| 19E | CFDNGKSYKIGEQWERPYLSGNRLECTCLGNGRGEFRC |
| 19F | CFDNGKSYKIGEQWERPYLSGNRLECTCLGNGSGRWQC |
| 19G | CHDEKTGSSYKIGETWERPYEGFMLSCTCLGNGSGRWQC |
| 19H | CHDEKTGSSYKIGEQWERPYLSGNRLECTCLGNGRGEFRC |
| 19I | CHDEKTGSSYKIGETWERPYEGFMLSCTCLGNGRGEFRC |

FIG. 19

| | | | | | 10 | | | | 20 | | | | 30 | | | 40 | | | 50 | | | 60 | | | 70 | | | 80 | |
|---|---|---|---|---|---|---|---|---|---|---|---|---|---|---|---|---|---|---|---|---|---|---|---|---|---|---|---|---|---|
| UK    | C | YEGNGHF | YRG | KASTDTM | G | RP | C | LP | W | NSATVLQQTYHAHRSDALQLG | L | GKH | NYCRNPD | NRR-RP | WC | YVQVGLKPLVQE | C | MVHD | C |
| tPAK1 | C | YEDQGIS | YRG | TWSTAES | G | AE | C | TN | W | NSSALAQKPYSGRRPDAIRLG | L | GNH | NYCRNPD | RDS-KP | WC | YVFKAGKYSSEF | C | STPA | C |
| tPAK2 | C | YFGNGSA | YRG | AHSLTES | G | AS | C | LP | W | NSHILIGKVYTAQMPSAQALG | L | GKH | NYCRNPD | GDA-KP | WC | HVLKNRRLTWEY | C | DVPS | C |
| PLK1  | C | KTGDGKN | YRG | TMSKTKN | G | IT | C | QK | W | SSTSPHRPRFSPATHPSE---G | L | EE- | NYCRNPD | NDPQGP | WC | YTTD-PEKRYDY | C | DILE | C |
| PLK2  | C | MHCSGEN | YDG | KISKTMS | G | LE | C | QA | W | DSQSPHAHGYIPSKFPNK---N | L | KK- | NYCRNPD | REL-RP | WC | FTTD-PNKRWEL | C | DIPR | C |
| PLK3  | C | LKGTGEN | YRG | NVAVTVS | G | HT | C | QH | W | SAWTPHTHNRTPENFPCK---N | L | DE- | NYCRNPD | GKR-AP | WC | HTT-NSQVRWEY | C | KIPS | C |
| PLK4  | C | YHGDGCQS | YRG | TSSTTTT | G | KK | C | QS | W | SSMTPHRHQKTPENYPNA---G | L | TM- | NYCRNPD | ADK-GP | WC | FTTD-PSVRWEY | C | NLKK | C |
| PLK5  | C | MFGNGKG | YRG | KRATTVT | G | TP | C | QD | W | AAQEPHRHSIFTPETNPRA---G | L | EK- | NYCRNPD | GDVGGP | WC | YTT-NPRKLYDY | C | DVPQ | C |
| FXII  | C | YDGRGLS | YRG | LARTTLS | G | AP | C | QP | W | ASEATYRNVTAEQARNW----G | L | GGH | AFCRNPD | NDIR-P | WC | FVLNRDRLSWEY | C | DLAQ | C |
| PTK1  | C | AEGLGTN | YRG | HVNITRS | G | IE | C | QL | W | RSRYPHKPEINSTTHPGA---D | L | QE- | NFCRNPD | SSNTGP | WC | YTTDPTVRR-QE | C | SIPV | C |
| PTK2  | C | VPDRGQQ | YQG | RLAVTTH | G | LP | C | LA | W | ASAQAKALSKHQDFNSAV---Q | L | VE- | NECRNPD | GDEEGV | WC | YVAGKPGD-FGY | C | DLNY | C |

FIG. 20

MODIFIED T-PA WITH KRINGLE-/REPLACED BY ANOTHER KRINGLE

CROSS-REFERENCE TO RELATED APPLICATION

This application is a continuation of U.S. application Ser. No. 07/058,217 filed Jun. 4, 1987, now abandoned.

TECHNICAL FIELD

The present invention relates to fibrinolytic agents, methods for their production, and pharmaceutical compositions containing them. More specifically, it relates to tissue plasminogen activator analogs having a modified kringle domain.

BACKGROUND ART

Blood coagulation is a process consisting of a complex interaction of various blood components which eventually gives rise to a fibrin network, or clot. Degradation of the fibrin network can be accomplished by activation of the zymogen plasminogen into plasmin. Plasmin is a serine protease which acts directly to degrade the fibrin network and thereby regulate the coagulation process. Conversion of plasminogen into plasmin is normally catalyzed in vivo by tissue-type plasminogen activator (t-PA), a fibrin-specific serine protease which is believed to be the physiological vascular activator of plasminogen. Urokinase-type plasminogen activator (u-PA) is another member of the class of plasminogen activators characterized as serine proteases. t-PA and u-PA are functionally and immunologically distinguishable.

t-PA normally circulates as a single polypeptide chain of $M_r \simeq 72,000$ daltons, which is converted to a two-chain form by cleavage of a peptide bond between amino acids 275 (Arg) and 276 (Ile). The heavy chain of t-PA (two variants of $M_r$ 40,000 and 37,000) is derived from the amino-terminus, while the light chain ($M_r$ 33,000) is derived from the carboxy-terminal end of the t-PA molecule. This cleavage is catalyzed by trypsin or plasmin, and is accompanied by an increase in activity as measured using synthetic substrates, and by an increase in fibrinolytic activity. Single-chain t-PA becomes active upon binding to fibrin, probably due to a conformational change in the activator induced by binding to fibrin. Cleavage to the two-chain form may be associated with rapid clearance of t-PA from the bloodstream, but conflicting reports on this have been published (see Wallen et al., *Eur. J. Biochem.* 132: 681-686, 1983), and the clearance mechanism is poorly understood.

A two-dimensional model of the potential precursor t-PA protein has been established (Ny et al., *Proc. Natl. Acad. Sci. USA* 81: 5355-5359, 1984). From this model, it was determined that the heavy chain contains two triple disulfide structures known as "kringles." Similar kringle structures also occur in prothrombin, plasminogen and urokinase, and are believed to be important for binding to fibrin (Ny et al., ibid.). The second kringle (K2) of t-PA is believed to have a higher affinity for fibrin than the first kringle (K1) (Ichinose, Takio and Fujikawa, personal communication; Verheijen, et al., *EMBO. J.* 5: 3525-3530, 1986).

In addition, the heavy chain of t-PA contains a "growth factor" domain, a triple disulfide-bonded structure which has homology to epidermal growth factor and to similar domains in protein C, factor VII, factor IX and factor X. It has been found that the growth factor domain participates in the rapid in vivo clearance of t-PA, and that deletion of the growth factor domain neither prevents the binding of the resultant molecule to fibrin nor blocks its ability to activate plasminogen.

The heavy chain of t-PA also contains a "finger" domain that is homologous to the finger domains of fibronectin. Fibronectin exhibits a variety of biological activities, including fibrin binding; its fibrin-binding activity has been correlated to four or five of its nine finger domains.

The light chain of t-PA contains the active site for serine protease activity, which is highly homologous to the active sites of other serine proteases.

The precursor form of t-PA additionally comprises a pre-region followed downstream by a pro-region, which are collectively referred to as the "pre-pro" region. The pre-region contains a signal peptide which is important for secretion of t-PA by vascular endothelial cells (Ny et al., ibid.). The pre sequence is believed responsible for secretion of t-PA into the lumen of the endoplasmic reticulum, a necessary step in extracellular secretion. The pro sequence is believed to be cleaved from the t-PA molecule following transport from the endoplasmic reticulum to the Golgi apparatus.

The use of t-PA for fibrinolysis in animal and human subjects has highlighted several shortcomings of the native molecule. The half-life of t-PA in vivo has been shown to be as short as three minutes in humans (Nilsson et al., *Scand. J. Haematol.* 33: 49-53, 1984). Injected t-PA is rapidly cleared by the liver, and, within 30 minutes, most of the injected material is metabolized to low molecular weight forms. This short half-life may limit the effectiveness of t-PA as a thrombolytic agent by necessitating high dosages. Typically, native t-PA is administered at a dose of 30-150 mg per patient, and the low solubility of the protein necessitates prolonged infusion. Fuchs et al. (*Blood* 65: 539-544, 1985) concluded that infused t-PA is cleared by the liver in a process independent of the proteolytic site, and that infused t-PA will not accumulate in the body, that is, the clearance mechanism cannot be saturated. Furthermore, doses of t-PA sufficient to lyse coronary thrombi are far larger than normal physiological levels, and may cause activation of plasminogen throughout the body, leading to systemic degradation of fibrinogen (Sherry, ibid.), which results in dangerous bleeding episodes. This systemic activity is apparently due to the low specificity of the two-chain form of the molecule.

Various workers have modified t-PA in attempts to enhance its clinical suitability. Rosa and Rosa (International Patent Application WO 86/01538) modified the Lys at position 277 of t-PA to stabilize the single-chain form of t-PA. Ile (277) t-PA produced in *E. coli* was found to be less active as a single-chain molecule, as compared to native t-PA. Wallen et al. (ibid.) postulated that this lysine residue may be responsible for proteolytic activity of single-chain t-PA. Heyneker and Vehar (published British Patent Application 2,173,804) disclose amino acid substitutions around the cleavage site of t-PA. A variant t-PA comprising Glu at position 275 was shown to have greater specific activity, as compared to native t-PA. This variant t-PA also formed fewer complexes with t-PA inhibitor. The single-chain form was also shown to have greater affinity for fibrin than the two-chain form. Robinson (WO 84/01786)

used enzymatic means to remove carbohydrate side chains from t-PA to increase plasma half-life. Van Zonneveld et al. (*Proc. Natl. Acad. Sci. USA* 83: 4670-4674, 1986) disclose modified forms of t-PA wherein portions of the heavy chain have been deleted. Robinson, et al. (EP 207,589 A1) disclose mutant forms of t-PA in which the growth factor domain has been deleted or otherwise modified. However, these variant forms of t-PA do not fully overcome the problems associated with the native protein.

There remains a need in the art for a plasminogen activating protein with a long plasma half-life and an enhanced affinity for fibrin. The present invention fulfills this need by providing novel derivatives of tissue plasminogen activator in which the kringle 1 domain has been replaced by a kringle domain derived from another protein. The t-pA analogs described herein provide significant advantages over native t-PA when used as therapeutic agents. These advantages include an enhanced specificity for fibrin, i.e., an enhanced affinity for fibrin which results in increased specificity for clot lysis. Increased specificity can reduce the systemic bleeding effects seen with native t-PA. Replacement of the kringle 1 domain may also be combined with other mutations in t-PA to provide additional novel analogs having enhanced clinical suitability. Through the use of recombinant DNA technology, a consistent and homogeneous source of these proteins is provided. The proteins can be utilized to lyse existing clots in heart attack and stroke victims and in others where the need to lyse or suppress the formation of fibrin matrices is therapeutically desirable.

DISCLOSURE OF THE INVENTION

Briefly stated, the present invention discloses tissue plasminogen activator analogs wherein the K1 domain of native t-PA is replaced with another kringle domain, the kringle domain mediating the binding of the analog to fibrin. The kringle contains six cysteine residues, and the analog exhibits greater specificity for fibrin than native t PA. Within selected embodiments of the present invention, the kringle domain is selected from the group consisting of the t-PA K2 domain, the plasminogen K1 domain, the plasminogen K4 domain, the plasminogen K5 domain, the factor XII kringle domain, the prothrombin K1 domain, and the prothrombin K2 domain. Within certain aspects of the present invention, the kringle domain may be composed of 78 to 82 amino acids, and may comprise the amino acid sequence:

Cys Lys Thr Gly X Gly Lys Asn Tyr Arg Gly Thr Met
   Ser Lys Thr Lys Asn Gly Ile Thr Cys Gln Lys Trp
   Ser Ser Thr Ser Pro His Arg Pro Arg Phe Ser Pro
   Ala Thr His Pro Ser Glu Gly Leu Glu Glu Asn Tyr
   Cys Arg Asn Pro Asp Asn Asp Pro Gln Gly Pro Trp
   Cys Tyr Thr Thr Asp Pro Glu Lys Arg Tyr Asp Tyr
   Cys Asp Ile Leu Glu Cys, wherein X is Asp or Asn.

The t-PA analogs described herein may further contain a substitution of at least one amino acid within thirteen amino acid residues of the cleavage site, this substitution resulting in an increased resistance to cleavage by plasmin. In addition, the t-PA analogs described herein may contain a finger domain having an amino acid sequence selected from the group consisting of the sequences set forth in FIGS. 19 (A)–(I).

Within other aspects of the present invention, the kringle domain may be the prothrombin K1 domain further modified to lack carbohydrate. In addition, the analogs described herein may further contain the K2 domain of native t-PA modified to contain serine and threonine at amino acid positions 183 and 186, respectively. Still further, the analogs described herein may lack a growth factor domain, or may contain a growth factor domain of a protein selected from the group consisting of native t-PA, protein C, factor VII, factor IX, and factor X. Within a particularly preferred embodiment, the growth factor domain is that of native t-PA, the growth factor domain being modified so that at least one cysteine residue is replaced with another amino acid. The amino acid is preferably serine or alanine.

Within certain preferred embodiments described herein, the cysteine residues are located at positions 1 and 22 relative to the N-terminus of the kringle domain, and at positions 1, 6, 18 or 19, and any of 29, 30 or 31 relative to the C-terminus of the kringle domain.

DNA sequences encoding the t-PA analogs described above, as well expression vectors containing such DNA sequences are also disclosed. Preferred expression vectors in this regard are Zem99-8000 or Zem99-8100.

Host cells transfected or transformed with such an expression vector are also disclosed. The host cell may be *E. coli* or a mammalian host cell, such as BHK host cells.

Still another aspect of the present invention disclosed a pharmaceutical composition comprising a t-pA analog as described herein, and a physiologically acceptable carrier or diluent.

These and other aspects of the present invention will become evident upon reference to the following detailed description and attached drawings.

BRIEF DESCRIPTION OF THE DRAWINGS

FIG. 1 illustrates the pre-pro t-PA coding sequence constructed from cDNA and synthesized oligonucleotides, together with the amino acid sequence of the encoded protein. Numbers above the lines refer to nucleotide position and numbers below the lines refer to amino acid position.

FIG. 3 illustrates the amino acid sequence and DNA sequence of the K1 domain of plasminogen.

FIGS. 9 and 10 show the cDNA sequences and amino acid sequences of representative t-PA analogs.

FIG. 15 shows the mutated t-PA sequence in plasmid Zem99-9100, together with the amino acid sequence of the encoded t-PA analog. Numbers refer to amino acid position.

FIG. 16 illustrates the nucleotide sequence of the mutant DNA sequence in Zem99-9200, together with the amino acid sequence of the encoded t-PA analog. Numbers refer to amino acid position.

FIG. 19(A)-(I) illustrates the amino acid sequences of the finger domain of native t-PA and of consensus finger domains.

FIG. 20 illustrates the homology among kringle domains of urokinase (U), native t-PA (tPA), plasminogen (PL), factor XII (FXII) and prothrombin (PT). (-) indicates a gap inserted to maximize sequence alignment.

BEST MODE FOR CARRYING OUT THE INVENTION

Figure 2:
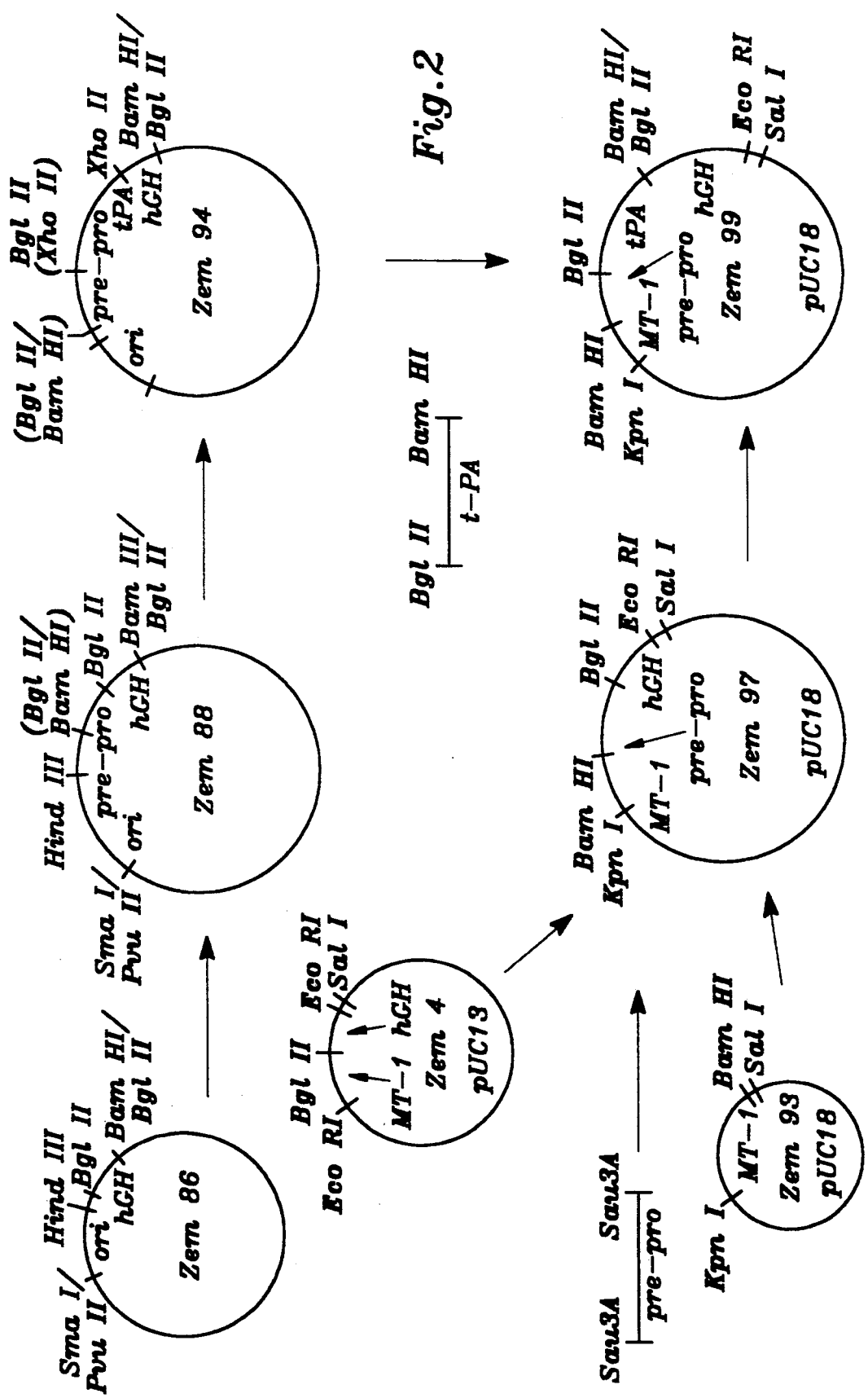
FIG. 2 illustrates the construction of the vector Zem99.

Prior to setting forth the invention, it may be helpful to an understanding thereof to set forth definitions of certain terms used herein.

Complementary DNA or cDNA: A DNA molecule or sequence which has been enzymatically synthesized from the sequences present in an mRNA template, or a clone of such a molecule.

DNA construct: A DNA molecule, or a clone of such a molecule, either single- or double-stranded, which has been modified through human intervention to contain segments of DNA combined and juxtaposed in a manner which would not otherwise exist in nature.

Plasmid or vector: A DNA construct containing genetic information which provides for its replication when inserted into a host cell. Replication may be autonomous or achieved by integration into the host genome. A plasmid generally contains at least one gene sequence to be expressed in the host cell, as well as sequences which encode functions that facilitate such gene expression, including promoters, transcription initiation sites and transcription terminators. It may be a linear molecule or a closed, circular molecule.

Pre-pro region: An amino acid sequence which generally occurs at the amino-termini of the precursors of certain proteins, and which is generally cleaved from the protein, at least in part, during secretion. The pre-pro region comprises, in part, sequences directing the protein into the secretory pathway of the cell, and generally contains a region which is rich in hydrophobic amino acids.

Domain: A three-dimensional, self-assembling array of amino acids of a protein molecule, which contains structural elements necessary for a specific biological activity of that protein.

Biological activity: The function or set of functions performed by a molecule in a biological context (i.e., in an organism, a cell, or an in vitro facsimile thereof). Biological activities of proteins may be divided into catalytic and effector activities. Catalytic activities of fibrinolytic agents often involve the activation of other proteins through specific cleavage of precursors. In contrast, effector activities include specific binding of the biologically active molecule to other molecules, such as fibrin, or to cells. Effector activity frequently augments, or is essential to, catalytic activity under physiological conditions. Catalytic and effector activities may, in some cases, reside in the same domain of the protein. For plasminogen activators, biological activity is characterized by the conversion of the pro-enzyme or zymogen plasminogen into plasmin, which in turn degrades fibrin matrices. Because fibrin acts as a cofactor in the activation of plasminogen by t-PA, single chain t-PA has relatively little activity in the absence of fibrin.

Native t-PA: A protein having the structure and biological activity of tissue plasminogen activator as isolated from human melanoma cells (see EP 0041766 A2). Native t-PA has the amino acid sequence of the melanoma cell t-PA or may contain slight variations in sequence. Such variations, arising from, for example, genetic polymorphisms, will not substantially alter the structure or activity of the protein. Native t-PA may be isolated from cells which naturally produce it, or may be prepared from recombinant cells which have been transfected or transformed with a DNA sequence encoding native t-PA. The amino acid sequence of a representative native t-PA is shown in FIG. 1.

t-PA analog: A protein having the characteristic biological activity of plasminogen activators as defined above, further characterized by the presence of a specific artificially induced mutation in the amino acid sequence. The DNA sequence encoding a t-PA analog is referred to as a "mutant DNA sequence," and will generally be in the form of a cDNA. The term "specific artificially induced mutation" includes deletions, insertions and substitutions in the amino acid sequence, which may be introduced through manipulation of a cloned DNA sequence. In general, the biological activity of the t-PA analogs will be measurably altered from that of native t-PA.

As discussed above, native t-pA contains two triple disulfide-bonded regions known as kringle domains, hereinafter referred to as "K1" and "K2." These domains are homologous to similar domains found in prothrombin, plasminogen, urokinase and other proteins and are believed to participate in the binding of t-PA to fibrin. The K2 domain has been shown to mediate the stimulatory effect of fibrin on the activation of plasminogen by native t-PA. The K1 domain of native t-PA may be characterized by the location and relationships of the cysteine residues. For purposes of the present invention, the K1 of native t-PA is defined as that portion of the protein from Cys (92) to Cys (173). This domain includes four other cysteine residues, the six cysteines being arranged in three intramolecular disulfide bonds. Bonds join cysteine residues 92 and 173, 113 and 155, and 144 and 168.

The disulfide-bonded structure described above is characteristic of kringle domains found in other proteins, including plasminogen, factor XII, and prothrombin. Positions of cysteine residues are highly conserved. There is also a strong preference for the sequence Tyr-Arg-Gly, Tyr-Asp-Gly, or Tyr-Gln-Gly at the position corresponding to residues 100–102 of native t-PA, Gly at the position corresponding to residue 110, Trp at the position corresponding to residue 116, Leu at the position corresponding to residue 138, and Trp at the position corresponding to residue 154. There is also a region of homology spanning residues 142–148 of native t-PA.

FIG. 20 illustrates the homology among kringle domains of urokinase, native t-PA, plasminogen, factor XII and prothrombin. In particular, there is a preference for Tyr-Arg-Gly, Tyr-Asp-Gly or Tyr-Gln-Gly at position 9 to 11 from the N-terminus; a Gly residue at position 19 from the N-terminus; a Trp at position 25 from the N-terminus; a Leu at one of positions 44 through 47 from the N-terminus; a Trp immediately N-terminal to the Cys at position 18 or 19 from the C-terminus; Arg-Asn-Pro-Asp immediately C-terminal to the Cys located at position 29-31 from the C-terminus; and any of Asn-Tyr, Asn-Phe or Ala-Phe located immediately N-terminal to the Cys at position 29-31 from the C-terminus.

The inventors have found that by replacing the K1 domain of native t-PA with a kringle domain derived from another protein, the fibrin affinity and specificity for clot lysis of the resulting protein are significantly enhanced. Suitable substitute kringle domains include the K1, K2, K3, K4 and K5 domains of plasminogen, the K2 domain of native t-PA, the K1 and K2 domains of prothrombin, and the kringle domain of factor XII. It is preferred to utilize the K1, K4 or K5 domain of plasminogen, with the K1 domain being particularly preferred. A partial cDNA sequence encoding plasminogen is disclosed by Malinowski et al., *Biochemistry* 23: 4243, 1984 This sequence may be used as a probe to obtain a full-length clone. The amino acid sequences of kringle domains of plasminogen are disclosed by Sottrup-Jensen et al., *Prog. Chem. Fibrinolysis Thrombolysis* 3: 191-209, 1978; Lerch et al., *Eur. J. Biochem.* 197: 7-13, 1980; and DeMarco et al., *J. Biol. Chem.* 257: 12716-12721, 1982. The amino acid sequence of the factor XII kringle domain is disclosed by McMullen and Fujikawa, *J. Biol. Chem.* 260: 5328-5341, 1985. DNA sequences encoding the various kringle domains may be obtained by enzymatic digestion of cDNA or, preferably, may be constructed from synthesized oligonucleotides based on the known amino acid or DNA sequences. Methods for synthesizing DNA are well known in the art. Alternatively, suitable oligonucleotides may be constructed from synthesized oligonucleotides based on the known amino acid or DNA sequences. Methods for synthesizing DNA are well known in the art. Alternatively, suitable oligonucleotides may be purchased from commercial suppliers.

According to the present invention, it is preferred to produce these novel proteins through the use of recombinant DNA technology, using cDNA clones or genomic clones as starting materials. Suitable DNA sequences can also be synthesized according to standard procedures. It is preferred to use cDNA clones because, by employing the full-length cDNA encoding native t-PA as starting material for producing modified t-PA, introns are removed so that all exons of the native t-PA are present and correctly oriented with respect to one another. The cDNA can also be used as a template for deletion, alteration or insertion of sequences via oligonucleotide-directed mutagenesis.

In addition to native t-PA, variants of t-PA, including those previously described, may be modified according to the present invention to contain a modified kringle domain. In this way, the benefits of the modified kringle domain can be combined with the advantages of the t-PA variants to give particularly useful products. For example, as described in detail in the examples which follow, the K1 domain of a t-PA analog which is resistant to cleavage by plasmin may be modified, resulting in a highly clot-specific plasminogen activator. t-PA analogs resistant to cleavage by plasmin were generated by altering the amino acid sequence around the Arg (275)-Ile (276) cleavage site of native t-PA. Such alterations are in the form of amino acid substitutions and additions, generally within thirteen amino acid residues of the cleavage site. Some of these alterations result in t-PA analogs which can be cleaved by thrombin. Also as described herein, the K1 modification may be combined with modifications in the finger domain, also resulting in a highly specific activator; or the growth factor domain of a t-PA analog having a modified kringle domain may be modified or deleted to increase plasma half-life. A preferred modification of the growth factor domain is the replacement of one or more of the cysteine residues with another amino acid. In addition, growth factor domains from proteins having long plasma half-lives may be substituted for the native t-PA growth factor domain. Substitute growth factor domains may be derived from, for example, protein C, factor VII, factor IX and factor X. DNA sequences encoding these proteins have been described (see, for example, Hagen et al., EP 200,421; Foster et al., *Proc. Natl. Acad. Sci. USA* 82: 4673-4677, 1985; Kurachi and Davie, *Proc. Natl. Acad. Sci. USA* 79: 6461-6464, 1982; and Leytus et al., *Biochemistry* 25: 5098-5102, 1986).

Other preferred modifications include the modification of carbohydrate attachment sites to alter glycosylation patterns of the t-PA analogs. Native t-PA contains a carbohydrate addition site in the K2 domain which is glycosylated to varying degrees (Pohl et al., *Biochemistry* 23: 3701-3707, 1984), leading to heterogeneity in preparations of the protein. This heterogeneity can be eliminated by altering the amino acid sequence, preferably by replacing Gly and Ser at positions 183 and 186, respectively, with Ser and Thr. These changes allow the production of a more uniform and soluble product. It has also been found that by blocking glycosylation on the K1 domain, plasma half-life of t-PA is enhanced. This is preferably achieved by replacing Ser (119) with Met. It is therefore desirable in t-PA analogs of the present invention to alter the K1 domain to block glycosylation if the K1 domain of the analog otherwise contains a carbohydrate addition site.

Recombinant DNA technology allows the convenient enhancement of the fibrin-binding domain of native t-PA. t-PA analogs having kringle substitutions as described above may be further modified by the insertion of additional kringle structures, the addition of finger domains, or the substitution of the finger domain. This methodology provides a means for selecting the optimum combination of functional domains found in native t-PA or in related proteins, and thus provides fibrinolytic agents with enhanced biological activity with respect to fibrin binding and specificity of serine protease activity.

Amino acid substitutions, additions or deletions are introduced by site-specific mutagenesis using the cloned t-PA DNA sequence or a portion thereof as a template. Techniques for oligonucleotide-directed in vitro mutagenesis are generally known in the art. A preferred such method is that of Zoller and Smith, *DNA* 3: 479-488, 1984. The mutated sequence is then joined to the remainder of the t-PA coding sequence, and the reconstructed (mutant) coding sequence is then inserted into an expression vector. The mutant sequences may be expressed in various host cells, including mammalian cells, yeast and other fungi, and bacteria.

Production of recombinant t-PA in bacteria, yeast, and mammalian cells is disclosed by, for example, Goeddel et al. (EP 93619 A1), Meyhack and Hinnen (EP 143,081 A2), and Gill (EP 174,835 A1). Methods for transfecting mammalian cells and for transforming bacteria and fungi with foreign DNA are well known in the art. Suitable expression vectors will comprise a promoter which is capable of directing the transcription of a foreign gene in a host cell and a functional transcription termination site.

In some instances, it is preferred that expression vectors further comprise an origin of replication, as well as sequences which regulate and/or enhance expression levels, depending on the host cell selected. Suitable expression vectors may be derived from plasmids, RNA and DNA viruses or cellular DNA sequences, or may contain elements of each.

Preferred prokaryotic hosts for use in carrying out the present invention are strains of the bacteria *Escherichia coli*, although *Bacillus* and other genera are also useful. Techniques for transforming these hosts, and for expressing foreign DNA sequences cloned in them, are well known in the art (see, for example, Maniatis et al., *Molecular Cloning: A Laboratory Manual*, Cold Spring Harbor Laboratory, 1982). Vectors used for expressing foreign DNA in bacterial hosts will generally contain a selectable marker, such as a gene for antibiotic resistance, and a promoter which functions in the host cell. Appropriate promoters include the trp (Nichols and Yanofsky, *Meth. in Enzymology* 101: 155, 1983), lac (Casadaban et al., *J. Bact.* 143: 971-980, 1980), TAC (Russell et al., *Gene* 20: 231-243, 1982), and phage γ promoter systems. Plasmids useful for transforming bacteria include pBR322 (Bolivar et al., *Gene* 2: 95-113, 1977), the pUC plasmids (Messing, *Meth. in Enzymology* 101: 20-77, 1983; and Vieira and Messing, *Gene* 19: 259-268, 1982), pCQV2 (Queen, *J. Mol. Appl. Genet.* 2: 1-10, 1983), and derivatives thereof.

Eukaryotic microorganisms, such as the yeast *Saccharomyces cerevisiae*, or filamentous fungi including *Aspergillus*, may also be used as host cells. Particularly preferred species of *Aspergillus* include *A. nidulans*, *A. niger*, *A. oryzae*, and *A. terreus*. Techniques for transforming yeast are described, for example, by Beggs (*Nature* 275 104-108, 1978). *Aspergillus* species may be transformed according to known procedures, for example, that of Yelton et al. (*Proc. Natl. Acad. Sci. USA* 81: 1740-1747, 1984). Expression vectors for use in yeast include YRp7 (Struhl et al., *Proc. Natl. Acad. Sci. USA* 76: 1035-1039, 1979), YEp13 (Broach et al., *Gene* 8: 121-133, 1979), pJDB248 and pJDB219 (Beggs, ibid.), and derivatives thereof. Such vectors will generally comprise a selectable marker, such as the nutritional marker TRP1, which allows selection in a host strain carrying a trp1 mutation. Preferred promoters for use in yeast expression vectors include promoters from yeast glycolytic genes (Hitzeman et al., *J. Biol. Chem.* 255: 12073-12080, 1980; Alber and Kawasaki, *J. Mol. Appl. Genet.* 1: 419-434, 1982; Kawasaki, U.S. Pat. No. 4,599,311) or alcohol dehydrogenase genes (Young et al., in *Genetic Engineering of Microorganisms for Chemicals*, Hollaender et al., eds., p 335, Plenum, N.Y., 1982; and Ammerer, *Meth. in Enzymology* 101: 192-201, 1983). To facilitate purification of a modified t-PA protein produced in a yeast transformant and to obtain proper disulphide bond formation, a signal sequence from a yeast gene encoding a secreted protein may be substituted for the t-PA pre-pro sequence. A particularly preferred signal sequence is the pre-pro region of the MFa1 gene (Kurjan and Herskowitz, *Cell* 30: 933-943, 1982; and Singh (EP 123,544)).

Higher eukaryotic cells may also serve as host cells in carrying out the present invention. Cultured mammalian cells, such as the BHK, CHO, NS-1, SP2/0, and J558L cell lines, are preferred. These and other cell lines are widely available, for example, from the American Type Culture Collection. A particularly preferred adherent cell line is the BHK cell line tk-ts13 (Waechter and Baserga, *Proc. Natl. Acad. Sci. USA* 79: 1106-1110, 1982), hereinafter referred to as "tk-BHK cells." Expression vectors for use in mammalian cells comprise a promoter capable of directing the transcription of a foreign gene introduced into a mammalian cell. Particularly preferred promoters include the SV40 promoter (Subramani et al., *Mol. Cell Biol.* 1: 854-64, 1981), the MT-1 promoter (Palmiter et al., *Science* 222: 809-814, 1983), and the mouse kappa gene promoter (Bergman et al., *Proc. Natl. Acad. Sci. USA* 81: 7041-7045, 1984). Also contained in the expression vectors is a transcription terminator, located downstream of the insertion site for the DNA sequence to be expressed. A preferred terminator is the human growth hormone (hGH) gene terminator (DeNoto et al., *Nuc. Acids Res.* 9: 3719-3730, 1981). In addition, vectors will preferably contain enhancer sequences appropriate to the particular host cell line.

For expression of mutant t-PAs in cultured mammalian cells, expression vectors containing cloned t-PA sequences are introduced into the cells by appropriate transfection techniques, such as calcium phosphate-mediated transfection (Graham and Van der Eb, *Virology* 52: 456-467, 1973; as modified by Wigler et al., *Proc. Natl. Acad. Sci. USA* 77: 3567-3570, 1980; or as described by Loyter et al., *Proc. Natl. Acad. Sci. USA* 79:422, 1982) or electroporation (Neumann et al., *EMBO J.* 1: 841-845, 1982). A small fraction of the cells integrate the DNA into the genome of the host cell or maintain the DNA in non-chromosomal nucear structures. These transfectants can be identified by cotransfection with a gene that confers a selectable phenotype (a selectable marker). Preferred selectable markers include the DHFR gene, which imparts cellular resistance to methotrexate (MTX), an inhibitor of nucleotide synthesis; or the bacterial neomycin resistance gene, which confers resistance to the drug G-418, an inhibitor of protein synthesis. After the host cells have taken up the DNA, drug selection is applied to select for a population of cells that are expressing the selectable marker at levels high enough to confer resistance. Selectable markers may be carried on the same vector as the sequence encoding the t-PA analog, or may be carried on a separate vector, depending on the transfection protocol employed.

The t-PA analogs of the present invention may be used within pharmaceutical compositions for the treatment of thrombosis. The parmaceutical compositions will comprise the t-PA analogs in combination with a carrier or diluent, such as sterile water or sterile saline, and may also comprise appropriate excipients and/or solvents. The resulting aqueous solutions may be packaged for use or filtered under aseptic conditions and lyophilized, the lyophilized preparation being combined with a sterile aqueous solution prior to administration.

Typically, an aqueous solution containing 3 g of mannitol and $10^6$ units of the t-PA analog is prepared under sterile conditions. One ml aliquots of this solution are pipetted into small vials, which are then lyophilized and sealed. For injection, the lyophilized material is combined with 2 ml of sterile water, the water being provided in a sealed ampoule. Administration is preferably by injection. The proteins of the present invention will typically be administered at doses of from about 6 mg to about 30 mg per patient, depending on the weight of the patient and the nature of the thrombus to be dissolved. However, the present invention is not restricted to the above range and the dose may be varied depending on the condition. Determination of proper dose will be apparent to the skilled practitioner.

EXAMPLES

Example 1—Construction of a Full-Length t-PA Clone

The sequence of a native human t-PA cDNA clone has been reported (Pennica et al., *Nature* 301: 214–221, 1983). The sequence encodes a pre-pro peptide of 32–35 amino acids followed by a 527–530 amino acid mature protein.

A cDNA clone comprising the coding sequence for mature t-PA was constructed using as starting material mRNA from the Bowes melanoma cell line (Rijken and Collen, *J. Biol. Chem.* 256: 7035–7041, 1981). This cDNA was then used to construct the plasmid pDR1296. *Escherichia coli* strain JM83 transformed with pDR1296 has been deposited with the American Type Culture Collection under Accession No. 53347.

Because the pre-pro sequence was not present in the cDNA clone pDR1296, it was constructed from synthesized oligonucleotides and subsequently joined to the cDNA. In the synthesized t-PA pre-pro sequence, cleavage sites for Bam HI and Nco I were introduced immediately 5' to the first codon (ATG) of the pre-pro sequence, and a Bgl II (Sau 3A, Xho II) site was maintained at the 3' end of the pre-pro sequence. The naturally-occurring pre-pro sequence lacks a convenient restriction site near the middle; however, the sequence GGAGCA (coding for amino acids -20 and -19, Gly Ala) can be altered to GGCGCC to provide a Nar I site without changing the amino acid sequence.

To construct the pre-pro sequence, the following oligonucleotides were synthesized using an Applied Biosystems Model 380-A DNA synthesizer:

ZC131: 5'GGA TCC ATG GAT GCA ATG AAG AGA GGG CTC TGC TGT GTG3'
ZC132: 5'TGG CGC CAC ACA GCA GCA GCA CAC AGC AGAG3'
ZC133: 5'GGC GCC GTC TTC GTT TCG CCC AGC CAG GAA ATC CATG3'
ZC134: 5'AGA TCT GGC TCC TCT TCT GAA TCG GGC ATG GAT TTC CT3'

Following purification, oligomers ZC131 and ZC132 were annealed to produce an overlap of 12 base pairs (Section 1). Oligomers ZC133 and ZC134 were similarly annealed (Section 2). The oligomers were mixed in Pol I buffer (Bethesda Research Labs), heated to 65° C. for five minutes, and slowly cooled to room temperature for four hours to anneal. Ten units of DNA polymerase I were added and the reaction proceeded for two hours at room temperature. The mixtures were electrophoresed on an 8% polyacrylamide-urea sequencing gel at 1,000 volts for 2½ hours in order to size fractionate the reaction products. The correct size fragments (those in which the polymerase reaction went to completion) were cut from the gel and extracted.

After annealing, Section 1 was cut with Bam HI and Nar I and cloned into Bam HI+Nar I-cut pUC8 (Vieira and Messing, *Gene* 19: 259–268, 1982; and Messing, *Meth. in Enzymology* 101: 20–77, 1983). Section 2 was reannealed and cut with Nar I and Bgl II and cloned into Bam HI+Nar I-cut pUC8. Colonies were screened with the appropriate labeled oligonucleotides. Plasmids identified as positive by colony hybridization were sequenced to verify that the correct sequence had been cloned.

Section 1 was then purified from a Bam HI+Nar I double digest of the appropriate pUC clone. Section 2 was purified from a Nar I+Xho II digest. The two fragments were joined at the Nar I site and cloned into Bam HI-cut pUC8.

The t-PA sequence of pDR1296 was then joined to the synthesized pre-pro sequence in the following manner (FIG. 2). Plasmid pIC19R (Marsh et al., *Gene* 32: 481–486, 1984) was digested with Sma I and Hind III. The ori region of SV40 from map position 270 (Pvu II) to position 5171 (Hind III) was then ligated to the linearized pIC19R to produce plasmid Zem67. This plasmid was then cleaved with Bgl II and the terminator region from the human growth hormone gene (De Noto et al., *Nuc. Acids Res.* 9: 3719–3730, 1981) was inserted as a Bgl II-Bam HI fragment to produce plasmid Zem86. The synthesized t-PA pre-pro sequence was removed from the pUC8 vector by digestion with Bam HI and Xho II. This fragment was inserted into Bgl II-digested Zem86 to produce plasmid Zem88. Plasmid pDR1296 was digested with Bgl II and Bam HI and the t-PA cDNA fragment was isolated and inserted into Bgl II-cut Zem88. The resultant plasmid was designated "Zem94."

The vector Zem99, comprising the MT-1 promoter, complete t-PA coding sequence, and the human growth hormone (hGH) terminator, was then assembled as shown in FIG. 2. A Kpn I-BAM HI fragment comprising the MT-1 promoter was isolated from MThGH111 ) Palmiter et al., *Science* 222:809–814, 1983) and inserted into pUC18 to construct Zem93. Plasmid EV142, comprising MT-1 and hGH sequences in the pBR322 derivative pBX322 (Palmiter et al., ibid.), was digested with Eco RI, and the fragment comprising the MT-1 promoter and hGH terminator sequences was isolated. This fragment was cloned into Eco RI-digested pCU13 to construct plasmid Zem4. Zem93 was then linearized by digestion with Bam HI and Sal I. Zem4 was digested with Bgl II and Sal I and the hGH terminator was purified. The t-PA pre-pro sequence was removed from the pUC9 vector as a Sau 3A fragment. The three DNA fragments were then joined, and a plasmid having the structure of Zem97 (FIG. 2) was selected. Zem97 was cut with Bgl II and the Bgl II-Bam HI t-PA fragment from pDR1296 was inserted. The resultant vector was designated Zem99.

Example 2: Construction of a DNA Sequence Encoding the K1 Domain of Plasminogen

Plasmid pK1 comprises a coding sequence for the K1 domain of plasminogen, the sequence of which is shown in FIG. 3. It was constructed from a series of eleven oligonucleotides designated "PK1-1, PK1-2, PK1-3–PK1-12," the sequences of which are shown in Table 1.

TABLE 1

| Oligonucleotide | Sequence |
|---|---|
| PK1-1 | 5'GAT CCA CGC GTG CCA CGT GCA AGA CCG GTG ATG GTA AAA ACT ACC GAG GTA CCA TGT CCA AGA CC3' |
| PK1-2 | 5'AAA AAC GGT ATT ACA TGT CAG AAA TGG TCA TCT ACT AGT CCA CAC CGG CCG CGG TTT TCT3' |
| PK1-3 | 5'CCA GCT ACC CAT CCA TCT GAA GGC CTG GAA GAG AAT TAC TGT AGG AAT CCA GAT AAC GAT3' |
| PK1-4 | 5'CCT CAG GGT CCC TGG TGT TAC ACC ACA GAC CCC GAG AAG AGG TAC GAC TAC TGC GAT ATC GCA TG3' |
| PK1-5 | 5'CCG TTT TTG GTC TTG G3' |
| PK1-6 | 5'GTA GCT GGA GAA AAC CG3' |
| PK1-7 | 5'CCC TGA GGA TCG TTA TC3' |
| PK1-9 | 5CGA TAT CGC AGT AGT CGT ACC TCT TCT C3' |
| PK1-10 | 5'GAT CCT CAG GGT CCC TGG TGT TAC ACC ACA3' |
| PK1-11 | 5'GAC CCC GAG AAG AGG TAC GAC TAC TGC GAT ATC GCA TG3' |
| PK1-12 | 5'GGG GTC TGT GGT GTA ACA CCA GGG ACC CTG AG3' |

The coding sequence for nucleotides 1 through 182 of the plasminogen K1 domain was constructed from oligonucleotides PK1-1 through PK1-7 in the following manner. 100 pmole each of the oligonucleotides PK1-1, PK1-2, PK1-3 and PK1-4 were phosphorylated at their 5' termini. The phosphorylated oligonucleotides were mixed with 100 pmole each of PK1-5, PK1-6, and PK1-7. The mixture was precipitated with ethanol and the precipitate was resuspended in H$_2$O and heated for three minutes at 90° C. The solution was then left to stand at room temperature for ten minutes, then placed on ice. To the chilled mixture was added 10 μl of 660 mM Tris HCl, pH 7.6, containing 6.6 mM MgCl$_2$, 10 μl of 0.1M dithiothreitol, 10 μl of 5 mM ATP, and 1000 units of T$_4$ DNA ligase. The mixture was incubated 15 hours at 14° C. Ethanol was added and the precipitate was resuspended in 20 μl of TE buffer (10 mM Tris HCl, 1 mm EDTA, pH 8.0), followed by the addition of an equal volume of alkali loading buffer (20 mM NaCl, 2 mM EDTA, 80% formamide, 0.1% xylene cyanol and 0.1% bromphenol blue). The mixture was heated for three minutes at 90° C. and electrophoresed on a 6% polyacrylamide gel containing 8.4M urea for one hour at 300 volts. The gel was stained with ethidium bromide, and a 250 bp band was recovered by electrophoretic transfer to DEAE-cellulose paper (Dretzen et al., *Anal. Biochem.* 112: 295-298, 1981). The recovered DNA was solubilized in 100 μl of TE buffer and the fragment was designated "PK1-n." PK1-n was C-tailed at the 3' terminus by combining 10 μl of the PK1-n solution with 2 μl of 100 mM sodium cacodylate—25 mM HEPES, pH 7.6, 6.2 μl of 1 mM dCTP, 10 units terminal deoxynucleotidyl transferase and 5 μl of H$_2$O. The reaction mix was incubated at 37° C. for ten minutes, then extracted with phenol:chloroform (1:1).

One μl of 3'-oligo (dG) tailed pUC9 (obtained from Pharmacia) was cleaved with Sma I. The linearized, tailed plasmid was added to the C-tailed PK1-n. The mixture was then ethanol-precipitated, and the DNA was resuspended in 0.5 μl of 2M KCl and 9.5 μl of TE buffer, and incubated at 65° C. for 10 minutes, then cooled to room temperature. To the cooled mixture were added 5 μl of 0.2M Tris HCl, pH 7.5, containing 0.1M MgCl$_2$ and 0.1M dithiothreitol, 20 μl of 2.5 mM dNTPs, 10 μl of 5 mM ATP, 53 μl H$_2$O, 5 units DNA polymerase I (Klenow fragment), and 300 units T$_4$ DNA ligase (final volume of 100 μl). The mixture was incubated at 14° C. for 12 hours, then used to transfect *E. coli* JM83.

Figure 4:
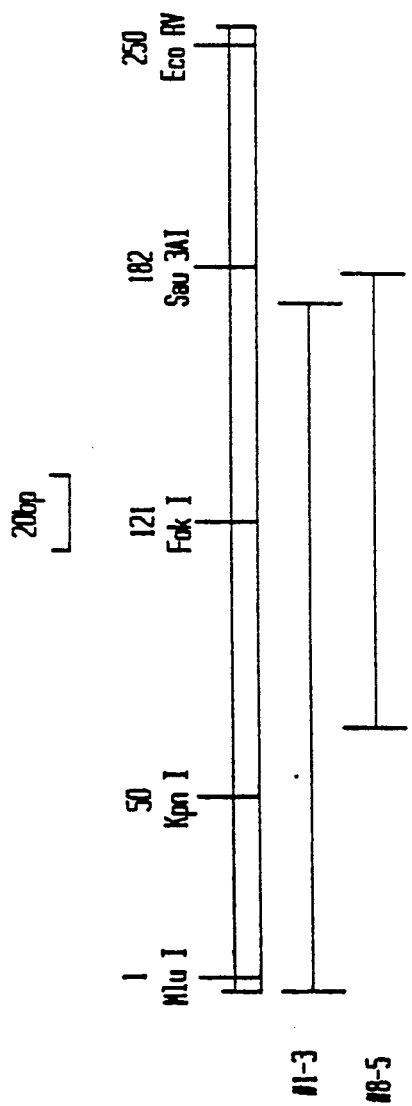
FIG. 4 shows partial restriction maps of clones #1-3 and #8-5, which encode portions of the plasminogen K1 domain.

The transfected JM83 cells were probed with PK1-6 using the method of Wallace et al. (*Nuc. Acids Res.* 9: 879-894, 1981). Twenty positive clones-were sequenced and two were selected, #1-3, including base pairs 1-170, and #8-5, including base pairs 68-186 (see FIG. 4).

Figure 5:
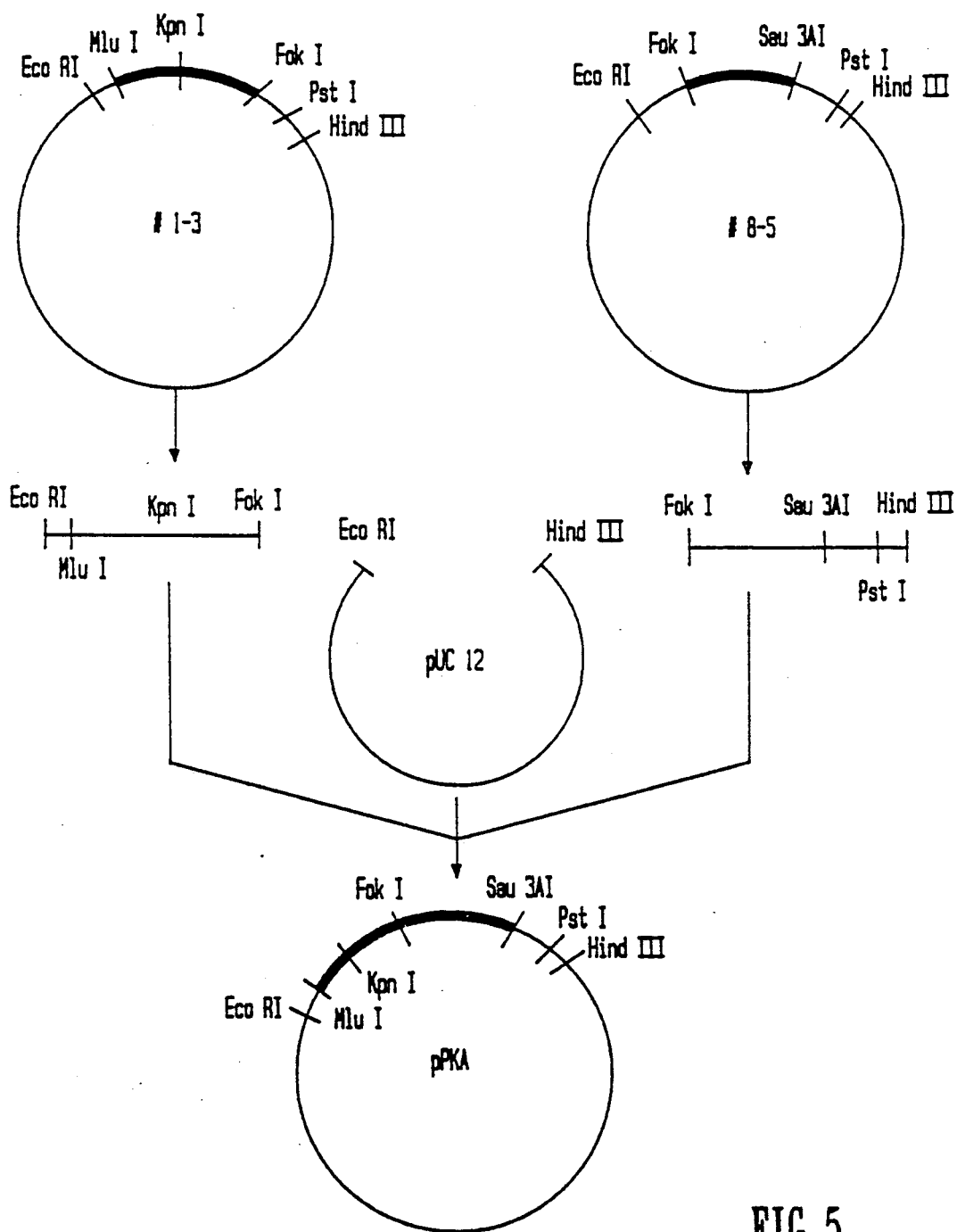
FIG. 5 illustrates the construction of plasmid pPKA.

Referring to FIG. 5, clone #1-3 was digested with Eco RI and Fok I, and a 130 bp fragment containing a Kpn I site was recovered. Similarly, clone #8-5 was digested with Fok I and Hind III, and a 90 bp fragment was recovered. The two fragments were joined to Eco RI, Hind III-digested pUC12, and the resultant plasmid was designated "pPKA." This plasmid thus contains a DNA sequence corresponding to nucleotides 1-182 of the plasminogen K1 sequence.

The remainder of the K1 sequence was constructed using oligonucleotides PK1-9, PK1-10, PK1-11 and PK1-12. One pmole each of the oligonucleotides was phosphorylated at the 5' end and the combined oligos were mixed with 40 ng of Bam HI, Sph I-digested M13tg130 RF (obtained from Amersham). To this mixture were added 4 μl of 660 mM Tris HCl, pH 7.6, containing 66 mM MgCl$_2$, and 22 μl of H$_2$O. The solution was heated for three minutes at 90° C. and allowed to cool to room temperature over a period of one hour. Four μl of 0.1M dithiothreitol, 4 μl of 5 mM ATP, and 300 units of T$_4$ DNA ligase were added, and the mixture was incubated for 12 hours at 14° C. The resulting phage clone, designated "M13PKB RF" (FIG. 6), contained nucleotides 183 through 250 of the K1 sequence.

Figure 6:
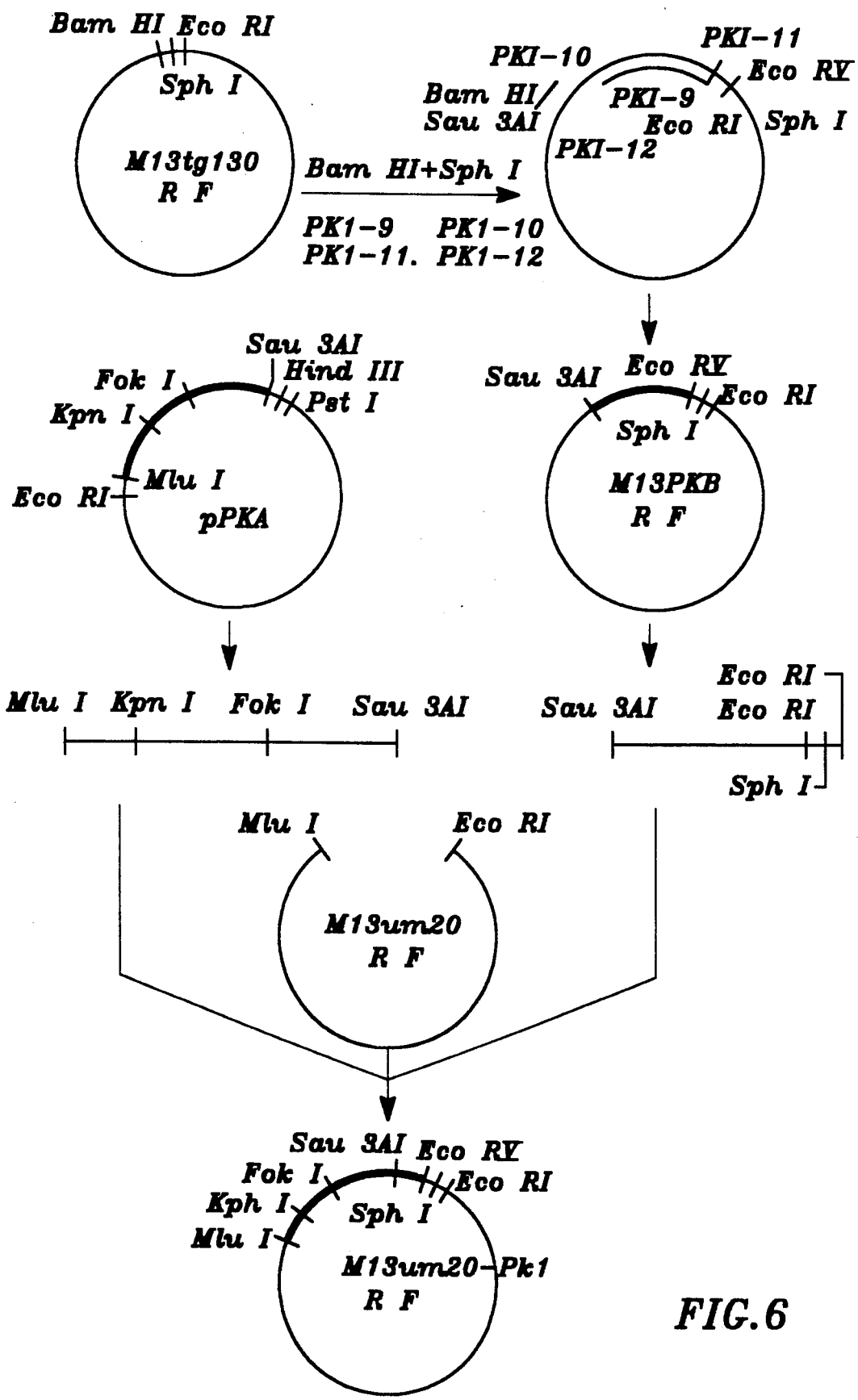
FIG. 6 illustrates the construction of a vector containing the plasminogen K1 coding sequence.

The assembly of the complete K1 coding sequence is illustrated in FIG. 6. Plasmid pPKA was digested with Mlu I and Sau 3AI, and a 176 bp fragment was recovered. M13PKB RF was digested with Sau 3AI and Eco RI, and an 88 bp fragment was recovered. These fragments were joined to Mlu I, Eco RI-digested M13um20 RF (obtained from IBI), and the resultant plasmid was designated "M13um20-PK1."

Figure 7:
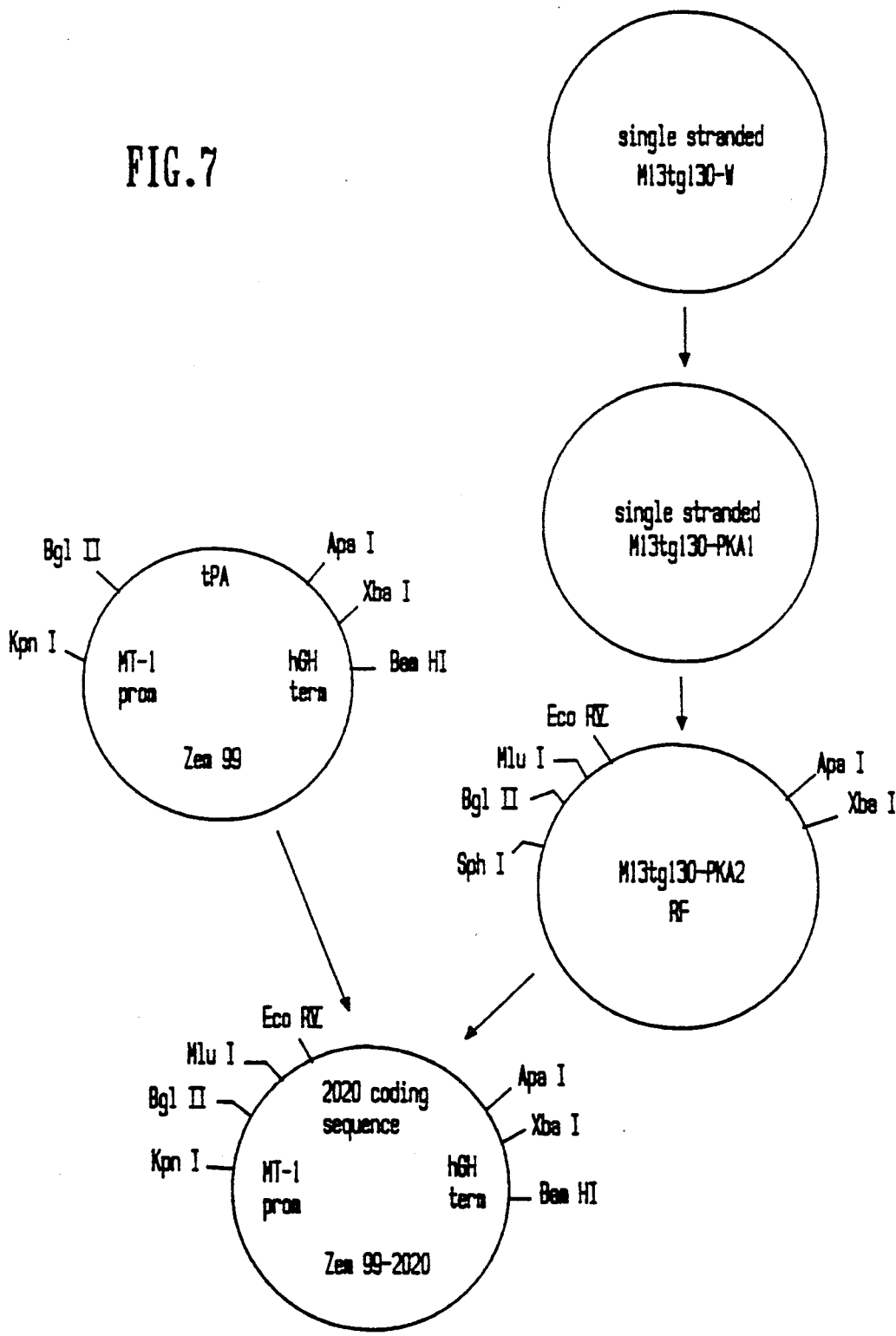
FIG. 7 illustrates the construction of plasmid Zem99-2020.
Figure 8:
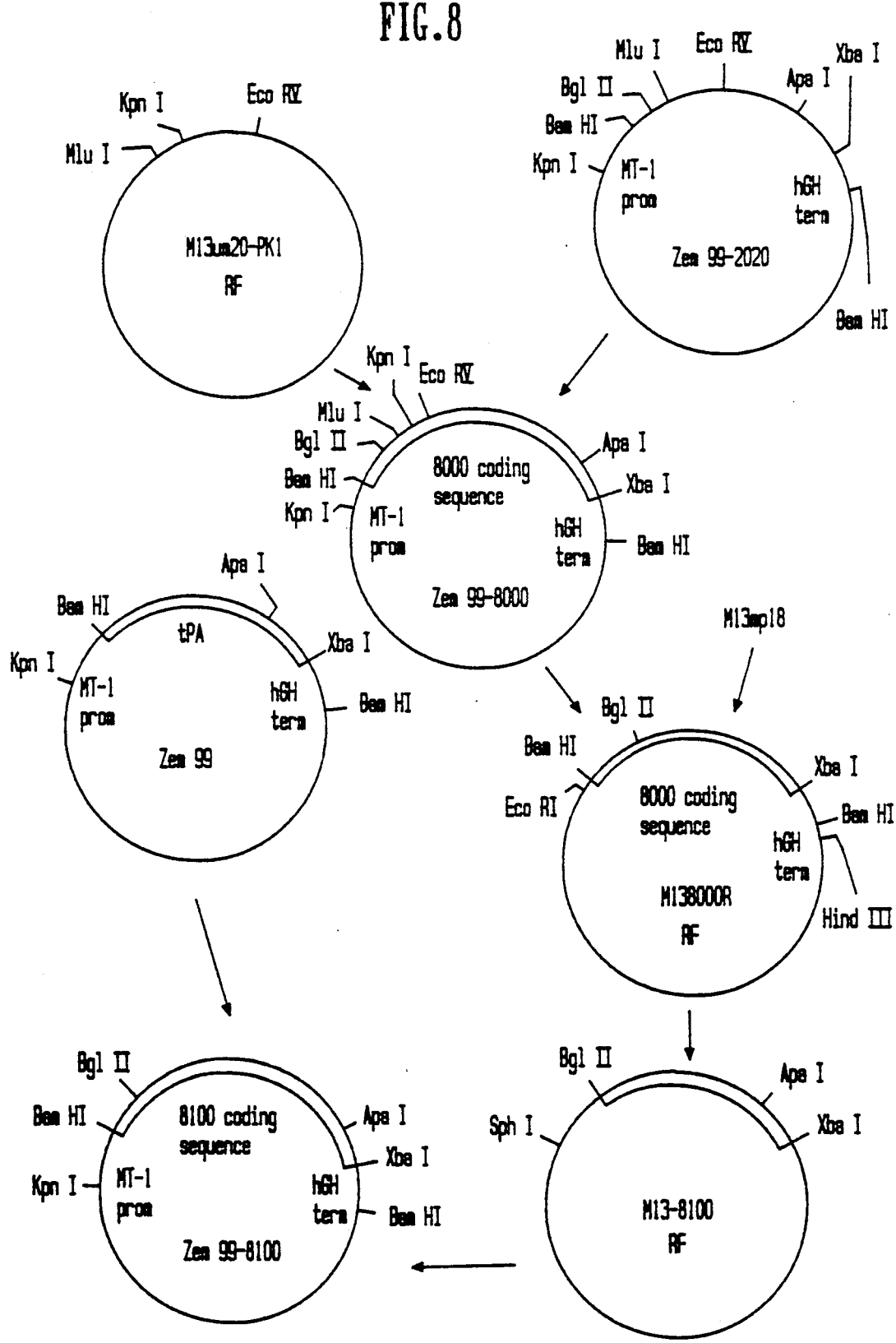
FIG. 8 illustrates the construction of the plasmids Zem99-8000 and Zem99-8100.

The PK1 coding sequence was then inserted into the t-PA cDNA as a replacement for the t-pA Kringle 1 sequence (FIGS. 7 and 8). The t-PA sequence was first mutagenized to insert Mlu I and Eco RV sites. Plasmid pDR1496 was digested with Sph I and Xba I, and the 2.1 kb fragment comprising the alpha factor and t-PA sequences was isolated. (*S. cerevisiae* strain E8-11c transformed with pDR1496 has been deposited with American Type Culture Collection under Accession Number 20728.) This fragment was joined to Sph I, Xba I-digested M13tg130 (RF), and the resultant phage was designated" M13tg130-W." Single-stranded phage DNA was then annealed to an oligonucleotide (5'GCA CGT GGC ACG CGT ATC TAT TTC3'), and mutagenesis was carried out according to standard procedures. The mutagenized phage was designated "M13tg130-PKA1." Single-stranded DNA of M13tg130-PKA1 was isolated and mutagenized with an oligonucleotide having the sequence 5'CTC AGA GCA TTC CAG GAT ATC GCA GAA CTC3'. Single-stranded DNA was prepared from the mutagenized phage and sequenced. A clone containing an Mlu I site at the 5' end and an Eco RV site at the 3' end of the Kringle 1 coding sequence was selected and designated "M13tg130-PKA2" (FIG. 7).

Replicative form DNA was prepared from M13tg130PKA2 and was digested with Bgl II and Apa I. The fragment containing the Mlu I and Eco RV sites was recovered and joined to Bgl II, Apa I-digested Zem99, as shown in FIG. 7. The resultant plasmid was designated "Zem99-2020."

The PK1 sequence was then inserted into the t-PA cDNA. M13um20-PK1 RF was digested with Mlu I and Eco RV, and the 336 bp fragment was recovered. This fragment was joined to Mlu I, Eco RV-digested Zem99-2020 to construct Zem99-8000 (FIG. 8). The mutant t-PA coding sequence of Zem99-8000 and the encoded amino acid sequence are shown in FIG. 9. *E. coli* transformed with Zem99-8000 has been deposited with the Fermentation Research Institute, Agency of Industrial Science and Technology, Ministry of International Trade and Industry, Japan (FRI), under Accession No. FERM BP-2160.

Plasmids Zem99-8000 and pSV2-dhfr (Subramani et al., ibid.) were used to cotransfect tk-BHK cells by the method of Loyter (*Proc. Natl. Acad. Sci. USA* 79: 422, 1982). Transfectants were cloned by the limiting dilution method. The mutant t-PA protein, designated "#8000," was affinity-purified on a column containing an antibody to native t-PA.

Example 3: Preparation of #8100

A second plasminogen K1 sequence encoding Asn at position 96 was constructed (FIG. 8). Zem99-8000 was digested with Bam HI, and the fragment containing the Bgl II site was recovered. This fragment was joined to Bam HI-cut M13mp18 to construct M13-8000R. An oligonucleotide primer (sequence 5'TTT TTA CCA TTA CCG GTC TT3') was annealed to single-stranded M13-8000R, and mutagenesis was carried out according to routine procedures. Clones were screened and sequenced, and double-stranded DNA, designated "M13-8000RF," was prepared from a positive clone. This phage was digested with Bgl II and Apa I, and the t-PA fragment was isolated and joined to Bgl II, Apa I-cut Zem99. The resultant plasmid was designated "Zem99-8100." The t-PA coding sequence present in Zem99-8100 and the encoded amino acid sequence are shown in FIG. 10. *E. coli* RR1 transformed with Zem99-8100 has been deposited with the Fermentation Research Institute under Accession No. FERM BP-2821.

To express the 8100 mutant protein, Zem99-8100 and pSV2-dhfr were used to cotransfect tk-BHK cells by the method of Loyter (ibid.). Transformants were cloned by the limiting dilution method. The protein was affinity-purified as described above.

Example 4—Substitutions of the K1 Domain in t-pA Analogs Resistant to Cleavage by Plasmin A: Mutagenesis For site-specific mutagenesis of the cleavage site, a 472 bp Eco RI fragment comprising the t-PA sequence from bp 802 to bp 1274 was isolated from Zem99 and cloned into the Eco RI site of M13mp18 (replicative form). The recombinant phage were transfected into *E. coli* (JM101), and anti-sense strand DNA was isolated.

Site-specific mutagenesis was then carried out on the single-stranded anti-sense template DNA using one of the mutagenic primers shown in Table 2 and ZC87 (5'TCC CAG TCA CGA CGT3') as second primer. Oligonucleotides ZC487, 488, 489 and 620 change the Phe at position 274 to Glu, Gly, Arg or Pro, respectively. Oligonucleotides ZC797, 874, 1013 and 1027 change the Arg at position 275 to Gly, Leu, Pro or Asp, respectively. Oligonucleotide 621 introduces a Leu in place of the Lys at position 277. Oligonucleotide 928 changes the Ile at position 276 to Pro. Oligonucleotide 875 changes Arg (275) to Leu and oligonucleotide 927 changes Phe (274) to Pro in the mutant which previously had Lys (277) converted to Leu. Thus, oligonucleotides 875 and 927 can be used to generate double mutations. Twenty pmoles of phosphorylated mutagenic primer and 20 pmoles of the second primer were combined with one pmole of single-stranded template in 10 μl of 20 mM Tris, pH 7.5, 10 mM MgCl$_2$, 50 mM NaCl, 1 mM DTT and incubated at 65° C. for 10 minutes, then 5 minutes at room temperature, and placed on ice. Ten μl of 20 mM Tris, pH 7.5, 10 mM MgCl$_2$, 2 mM ATP, 10 mM DTT containing 1 mM dNTPs, 2.5 units Klenow polymerase, and 3.5 units DNA ligase were added to the annealed DNA, and the mixture was incubated 3 hours at 15° C. The DNA was then transfected into competent *E. coli* JM101, and the cells were plated on YT agar and incubated at 37° C. The DNA was then transferred to nitrocellulose and prehybridized at the Tm-4° C. of the mutagenic primer for 1 hour in 6x SSC, 10x Denhardt's and hybridized to $^{32}$P-labeled mutagenic primer at Tm-4° C. in the same solution. After three washes at Tm-4° C., filters were exposed to X-ray film overnight. Additional wash steps were performed at 5° C. higher increments as necessary to identify mutant plaques. The mutated inserts were sequenced by the dideoxy method.

TABLE 2

| | |
|---|---|
| ZC487 | 5'CAG CCT CAG GAG CGC ATC AAA3' |
| ZC488 | 5'CAG CCT CAA GGT CGC ATC AAA3' |
| ZC489 | 5'CAG CCT CAG AGA CGC ATC AAA3' |
| ZC620 | 5'CAG CCT CAG CCT CGC ATC AA3' |
| ZC621 | 5'TTT CGC ATC CTC GGA GGG CTC3' |
| ZC797 | 5'CTT CAG TTC GGC ATC AAA3' |
| ZC874 | 5'CT CAG TTT CTC ATC AAA GG3' |
| ZC875 | 5'CT CAG TTT CTC ATC CTC GG3' |
| ZC927 | 5'CAG CCT CAG CCT CGC ATC CT3' |
| ZC928 | 5'CAG TTT CGC CCC AAA GGA GG3' |
| ZC1013 | 5'CT CAG TTT CCC ATC AAA GG3' |
| ZC1027 | 5'CCT CAG TTT GAC ATC AAA GG3' |

B: Vector Construction

Figure 11:
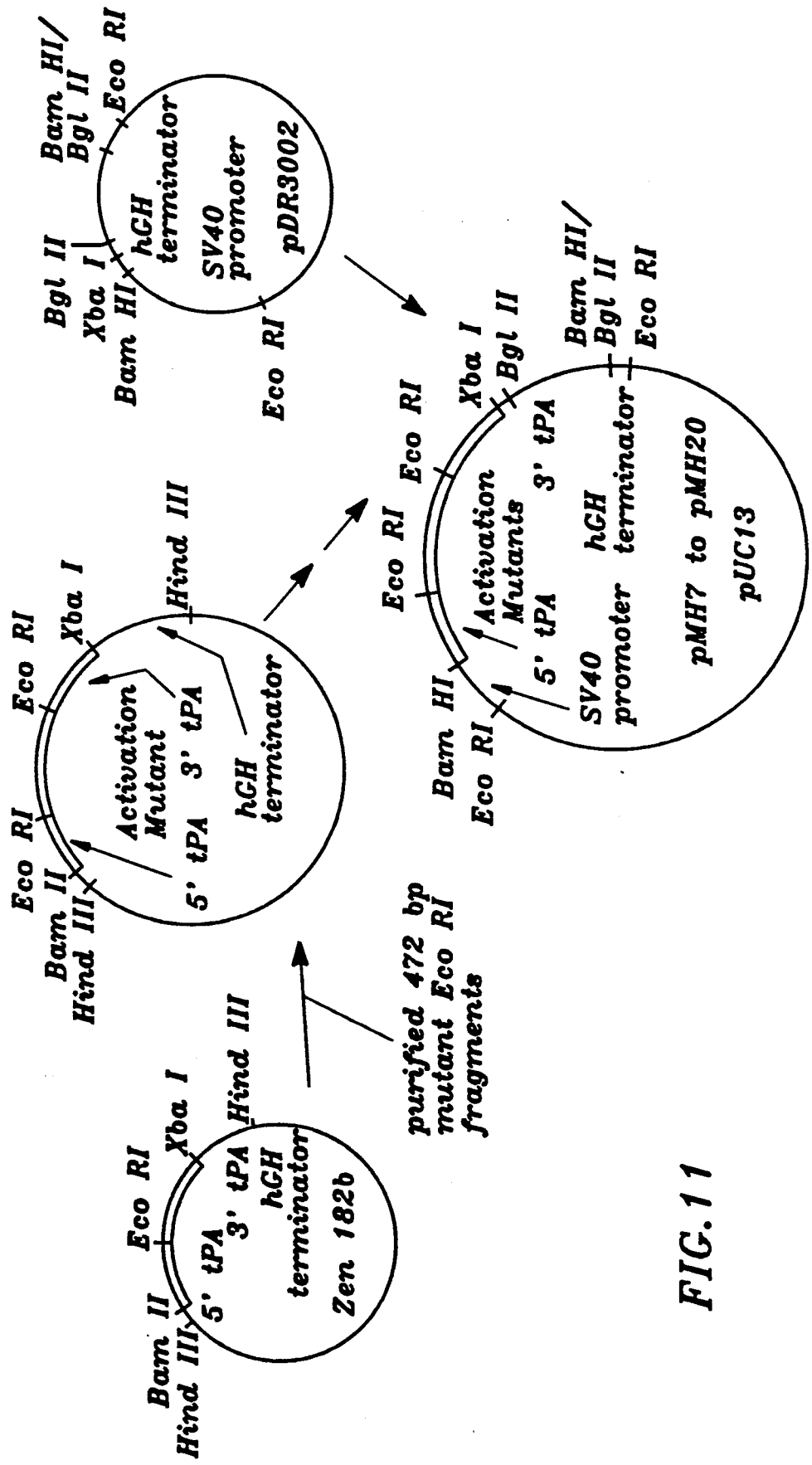
FIG. 11 illustrates the construction of the pMH series of plasmids, comprising mutant DNA sequences encoding t-PA analogs with altered cleavage sites.

Expression vectors for the altered sequences were then constructed (FIG. 11). Plasmid Zem86 (described in Example 1) was digested with Hind III and the ends filled in using DNA polymerase I (Klenow fragment). The linearized DNA was then digested with Eco RI; and a ~350 bp fragment, comprising the SV40 ori sequence, was gel-purified and ligated to Sma I+Eco RI-digested pUC13. The resultant vector was designated "pDR3001." Plasmid pDR3001 was digested with Sal I and Eco RI; and the ~350 bp fragment, comprising SV40 ori and poylinker sequences, was gel-purified. Zem86 was partially digested with Eco RI and completely digested with Xho I to remove the SV40 ori sequence. The SV40 fragment from pDR3001 was then joined to the linearized Zem86. The resultant plasmid was designated "pDR3002" (FIG. 11).

Figure 12:
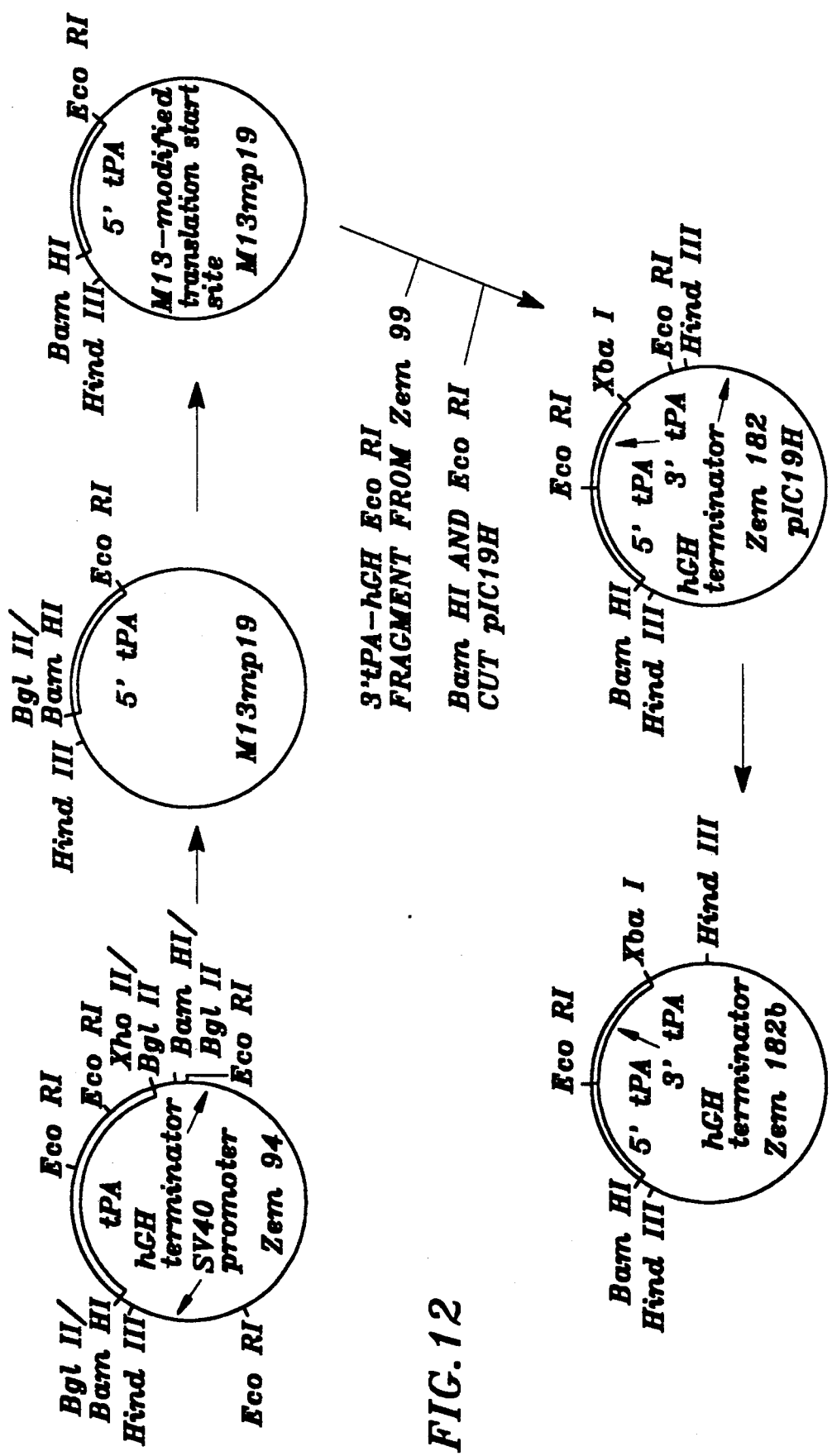
FIG. 12 illustrates the construction of the plasmid Zem182b.

The sequence just upstream of the ATG start codon of the t-PA sequence in Zem94 was altered by site-specific mutagenesis, resulting in the positioning of Hind III and Bam HI sites adjacent to the ATG. The resultant nucleotide sequence contains an adenine in the -3 position. Single-stranded M13 template DNA was prepared by inserting a ~800 bp Hind III-Eco RI fragment from Zem94 comprising polylinker, pre-pro, and a portion of the mature t-PA sequences into M13mp19. Site-specific mutagenesis was carried out essentially as described by Zoller et al. (*Manual for Advanced Techniques in Molecular Cloning Course*, Cold Spring Harbor Laboratory, 1983), using the oligonucleotide ZC444 (5'CAT CCA TGG TGG ATC CAA GCT TGG C3') as mutagenic primer. Oligonucleotide ZC87 (5'TCC CAG TCA CGA CGT3') was used as second primer. The mutated inserts were sequenced by the dideoxy method, and a clone in which polylinker sequences had been deleted and the Bam HI site at the 5' end of the pre-pro sequence had been restored was selected. This phage clone was digested with Bam HI and Eco RI, and the 5' t-PA sequence was isolated. Zem99 was digested with Eco RI, and the fragment comprising the 3' portion of the t-PA sequence and the hGH terminator was isolated. The two fragments were then joined with Bam HI + Eco RI-digested pIC19H (Marsh et al., *Gene* 32: 481–486, 1984) in a three-part ligation. A plasmid containing the t-PA fragments in the proper orientation was selected and designated "Zem182." Plasmid Zem182 was partially digested with Eco RI, and the ends were filled using DNA polymerase I (Klenow fragment). The linearized plasmid was gel-purified and recirculated using T4 DNA ligase. A plasmid in which the Eco RI site at the 3' end of the hGH terminator was destroyed was selected and designated "Zem182b" (FIG. 12).

Replicative form (RF) DNA was prepared from the mutagenized phage described in Example 4A, and the modified t-PA sequences were purified as Eco RI fragments. Plasmid Zem182b was digested with Eco RI, the vector sequences containing the 5' and 3' portions of the t-PA coding sequence were treated with calf alkaline intestinal phosphatase, and the modified t-PA sequences were inserted. The resultant plasmids were digested with Bam HI and Xba I, and the t-PA fragments were inserted into Bam HI + Xba I-cut pDR3002. The resultant vectors were designated "pMH7" through "pMH20" (Table 3 and FIG. 11).

TABLE 3

| Protein | Sequence of Amino Acids 273-279 |
|---|---|
| Native t-PA | Gln—Phe—Arg—Ile—Lys—Gly—Gly |
| pMH7 | Gln—Gly—Arg—Ile—Lys—Gly—Gly |
| pMH8 | Gln—Phe—Arg—Ile—Leu—Gly—Gly |
| pMH9 | Gln—Arg—Arg—Ile—Lys—Gly—Gly |
| pMH10 | Gln—Pro—Arg—Ile—Lys—Gly—Gly |
| pMH11 | Gln—Glu—Arg—Ile—Lys—Gly—Gly |
| pMH12 | Gln—Phe—Lys—Ile—Lys—Gly—Gly |
| pMH13 | Gln—Phe—Gly—Ile—Lys—Gly—Gly |
| pMH14 | Gln—Pro—Arg—Ile—Leu—Gly—Gly |
| pMH15 | Gln—Phe—Leu—Ile—Lys—Gly—Gly |
| pMH16 | Gln—Phe—Leu—Ile—Leu—Gly—Gly |
| pMH17 | Gln—Phe—Arg—Pro—Lys—Gly—Gly |
| pMH18 | Gln—Phe—Pro—Ile—Lys—Gly—Gly |
| pMH19 | Gln—Phe—Asp—Ile—Lys—Gly—Gly |

TABLE 3-continued

| Protein | Sequence of Amino Acids 273-279 |
|---|---|
| pMH20 | Gln—Phe—Gly—Ile—Leu—Gly—Gly |

The activation site mutations of pMH10, pMH13 and pMH17 are combined with the 8100 mutation disclosed in Example 3 to produce t-pA analogs having substantially increased specificity of clot binding and lysis. Vectors containing coding sequences for these analogs are constructed by combining, in a three-part ligation, the vector fragment from Bam HI, Xba I-digested Zem219b, the Bam HI-Apa I kringle fragment from Zem99-8100 and the Apa I-Xba I activation site fragment from the appropriate pMH vector. The resultant plasmids are used to transfect tk-BHK cells by electroporation. After selection and scale-up, the mutant proteins are purified and characterized.

Example 5—t-PA Analogs Having Substitutions in the K1 and Finger Domains

Replacement of the t-PA finger domain with a consensus finger region results in the elimination of potential proteolytic cleavage sites at Arg-27 and Lys-49. Eight finger replacement sequences were constructed, based on an analysis of the finger domains of fibronectin and t-PA. The amino acid sequences of these "consensus" finger domains are shown in FIG. 19 and Table 4.

The consensus finger sequences were constructed from oligonucleotides as described below, then inserted into the t-PA coding sequence. To facilitate this insertion, a Kpn I site was introduced downstream (3') of the region encoding the wild-type finger domain. Digestion of the resulting sequence with Bgl II and Kpn I resulted in the deletion of the finger domain.

A. Kpn I Site Insertion Between the Finger and Growth Factor Domains

In order to place a Kpn I site after the finger domain in t-PA, a mutagenesis was performed with oligonucleotide ZC986 (5'TTT GAC AGG TAC CGA GTG GCA3'). DNA of a phage M13 clone containing the 5' Bam HI-Eco RI fragment of the native t-PA cDNA was prepared. 100 μl of the DNA solution was used to infect *E. coli* RZ1032 in 100 μl of YT medium supplemented with 0.1 μg/ml uridine. This culture was incubated at 37° C., with vigorous shaking, overnight. Growing the M13 in RZ1032 produces phage containing uridine which are viable in RZ1032 but not in JM101.

The cells were spun out, and the phage supernatant was used to reinfect *E. coli* RZ1032. This second passage was performed to dilute out any JM101-derived phage which contained no uracil. Again, the cells were spun out and the phage were plated on JM101 and RZ1032. Normal viability was observed on RZ1032 plates (indicating phage at $10^9$ pfu/ml), but no plaques were observed on JM101 cells. A complementary strand primed with the mutagenic oligonucleotide was then produced in vitro. The new strand, containing the mutation, contained thymidine and was therefore viable in JM101; the wild-type template was not.

Template DNA was prepared by PEG precipitation of the phage supernatant followed by phenol-chloroform extraction and ethanol precipitation. One μg of this template DNA was hybridized with 10 μg of oligonucleotide ZC986 by briefly boiling, incubating at 65° C. for 5 minutes, and then slowly bringing the temperature down to 4° C. before adding 10 μl 0.2M HEPES, pH 7.8, 2 μl 100 mM DTT, 1 μl 1M MgCl$_2$, 20 μl 2.5 mM each dNTP, 10 μl 10 mM ATP, 1 μl 2.5 U/μl Klenow, and 2 μl 1 U/μl T$_4$ DNA ligase, final volume adjusted to 100 μl with H$_2$O. After extension at 37° C. for 2 hours, the DNA was transfected into competent JM101 cells. A control extension (minus oligonucleotide) was performed to compare the amount of background produced by extension by priming on contaminating RNA or DNA species. The transfection produced zero plaques with unmutagenized template, 150 on control extension (minus oligonucleotide) and 300 with mutagenized template.

The plates were screened by hybridizing a plaque lift with $^{32}$P-labeled mutagenic oligonucleotide and washing in 3M TMACl (Wood et al., *Proc. Natl. Acad. Sci. USA* 82: 1585-1588, 1985) at Tm-5° C. for 30 minutes and also by sequencing randomly picked plaques. One positive clone was obtained.

B. Production of Finger Replacement Domains

The consensus finger region replacements shown in Table 4 and FIG. 19 were constructed.

each with polynucleotide kinase at 37° C. for ½ hour. Then the indicated eight combinations (ABC, DEF, ABF, AEC, AEF, DBF, DEC and DBC) were produced by mixing the appropriate oligonucleotides, adding DNA ligase, and incubating at 37° C. for 1 hour. The products of this reaction were sorted out on a 6% polyacrylamide-8M urea sequencing gel. The bands corresponding to the DNA coding for full-length finger domains were cut out, and the DNA was eluted in 2.5M ammonium acetate. The DNA was ethanol-precipitated and resuspended in water to a concentration of 1 pmole/μl.

RF DNA was prepared from the positive clone described in Example 5A, and the Bam HI to Eco RI t-PA fragment was purified. Plasmid Zem219a (described in Example 5D, below) was digested with Xba I and then partially digested with Eco RI. The 1010 bp fragment, containing the 3' t-PA coding region, was purified. Plasmid Zem219b (described in Example 5D, below) was digested with Bam HI and Xba I and ligated to the 5' t-PA fragment (Bam HI-Eco RI) and the 1010 bp Eco RI-Xba I fragment. The resulting vector, designated "Zem238," contains a Kpn I site after the finger domain. Zem238 was digested with Bgl II and Kpn I,

TABLE 4

| Finger | Encoded Amino Acid Sequence | Oligonucleotides* |
|---|---|---|
| t-PA wild-type: | CRDEKTQMIYQQHQSWLRPVLR—SNRVEYCWC—N—SGRAQC | |
| Consensus 1: | CFD—NGKSYKIGETWERPYE—GFMLS—CTCLGNGRGEFRC | (ABC) |
| Consensus 2: | CHDEKTGSSYKIGEQWERPYL—SGNRLE—CTCLGNGSGRWQC | (DEF) |
| Consensus 3: | CFD—NGKSYKIGETWERPYE—GFMLS—CTCLGNGSGRWQC | (ABF) |
| Consensus 4: | CFD—NGKSYKIGEQWERPYL—SGNRLE—CTCLGNGRGEFRC | (AEC) |
| Consensus 5: | CFD—NGKSYKIGEQWERPYL—SGNRLE—CTCLGNGSGRWQC | (AEF) |
| Consensus 6: | CHDEKTGSSYKIGETWERPYE—GFMLS—CTCLGNGSGRWQC | (DBF) |
| Consensus 7: | CHDEKTGSSYKIGEQWERPYL—SGNRLE—CTCLGNGRGEFRC | (DEC) |
| Consensus 8: | CHDEKTGSSYKIGETWERPYE—GFMLS—CTCLGNGRGEFRC | (DBC) |

*A = ZC1116/1117
B = ZC1118/1119
C = ZC1120/1121
D = ZC1122/1123
E = ZC1124/1125
F = ZC1126/1127

TABLE 5

ZC1116
GAT CTT ATC AAG TCA TAT GTT TTG ATA ATG GAA AAT CTT ATA A
ZC1117
CTC CAA TTT TAT AAG ATT TTC CAT TAT CAA AAC ATA TGA CTT GAT AA
ZC1118
AAT TGG AGA AAC ATG GGA ACG GCC GTA TGA AGG ATT TAT GCT TTC T
ZC1119
CAT GTA CAA GAA AGC ATA AAT CCT TCA TAC GGC CGT TCC CAT GTT T
ZC1120
TGT ACA TGC CTA GGA AAT GGC CGC GGA GAA TTT AGA TGT CAT TCG GTA C
ZC1121
CGA ATG ACA TCT AAA TTC TCC GCG GCC ATT TCC TAG G
ZC1122
GAT CTT ATC AAG TCA TAT GTC ATG ATG AAA AAA CAG GCT CGA GTT ATA A
ZC1123
CTC CAA TTT TAT AAC TCG AGC CTG TTT TTT CAT CAT GAC ATA TGA CTT GAT AA
ZC1124
AAT TGG AGA ACA ATG GGA ACG GCC GTA TCT TTC TGG AAA TCG ATT AGA A
ZC1125
CAT GTA CAT TCT AAT CGA TTT CCA GAA AGA TAC GGC CGT TCC CAT TGT T
ZC1126
TGT ACA TGC CTA GGA AAT GGT TCC GGA AGA TGG CAA TGT CAT TCG GTA C
ZC1127
CGA ATG ACA TTG CCA TCT TCC GGA ACC ATT TCC TAG G

The eight consensus sequences were generated from the indicated oligonucleotides. The oligonucleotides (Table 5) were produced using an Applied Biosystems Model 380A DNA synthesizer. First, the twelve oligonucleotides were kinased and simultaneously labeled to a low specific activity with γ-$^{32}$P ATP by incubating gel-purified to remove the wild-type finger domain, and ligated with each of the eight consensus sequences to generate expression vectors 238-Fcon 1 to 238-Fcon 8.

C. t-PA Analogs Having a Substituted K1 Domain in Combination with a Consensus Finger Domain Single-stranded M13-8100 DNA is used as a template for mutagenesis with oligonucleotide ZC986 (Example 5A) to insert a Kpn I site at the 3' end of the finger region as described above. A correct clone (M13-8100-K) is identified by sequencing, and the RF DNA is digested with Kpn I and Xba I to isolate the mutant K1 fragment. The mutant K1 fragment is then inserted into Kpn I, Xba I-digested plasmids 238-Fcon 1 to 238-Fcon 8. Resultant plasmids 8100-F1 through 8100-F8 are transfected into tk-BHK cells by electroporation. The mutant proteins are purified and characterized.

D. Construction of Zem219b

Figure 13:
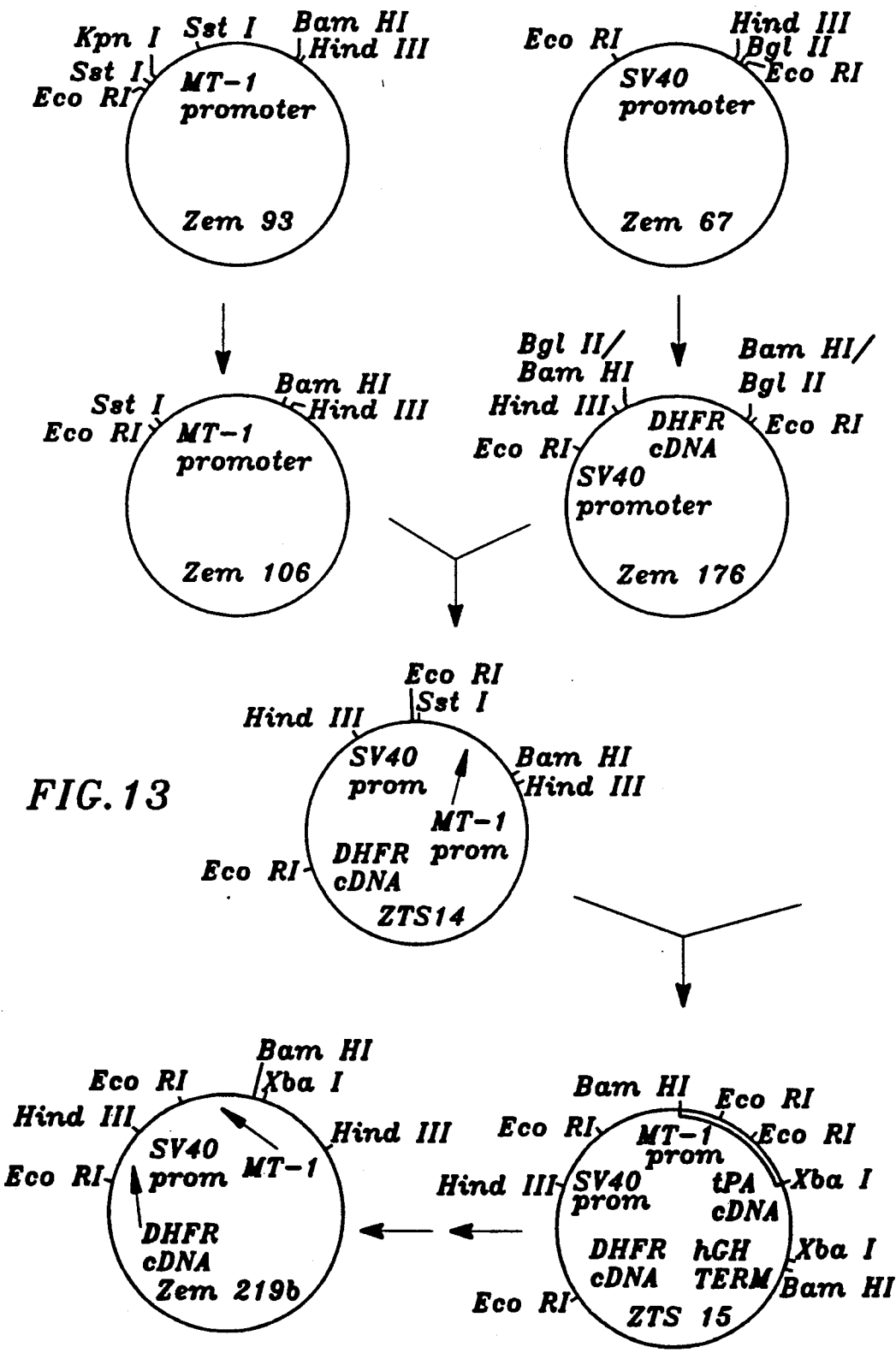
FIG. 13 illustrates the construction of plasmid Zem219b.

Plasmid pSV2-DHFR (Subramani et al., ibid.) was digested with Cfo I, and the fragment containing the DHFR cDNA and the 3' attached SV40 sequences was isolated, repaired, and ligated to Bam HI linkers. After digestion with Bam HI, an approximately 800 bp fragment containing the entire cDNA and the SV40 terminator region was purified and ligated to Bam HI-digested pUC8. Zem67 (Example 1) was digested with Bgl II and ligated with the Bam HI DHFR-SV40 fragment to generate plasmid Zem176. Plasmid Zem93 was digested with Sst I and re-ligated to generate plasmid Zem106, in which approximately 600 bp of sequence 5' to the MT-1 promoter were eliminated. Plasmid Zem106 was digested with Eco RI and ligated to the Eco RI fragment containing the DHFR gene from plasmid Zem176. The resulting plasmid was designated "Zts14." Plasmid Zts14 was digested with Bam HI and ligated to the Bam HI fragment from plasmid Zem99 containing the entire t-PA coding region and hGH terminator sequence. The resulting plasmid was designated "Zts15." Zts15 was partially digested with Bam HI, repaired, re-ligated and transformed to generate plasmid Zem219, in which the 3' Bam HI site was destroyed. Plasmid Zem219 was partially digested with Xba I, repaired, re-ligated and transformed to generate plasmid Zem219a, in which the 3' Xba I site was destroyed. Plasmid Zem219a was digested with Bam HI and Xba I, the vector sequences purified away from the t-PA cDNA sequences, and ligated with an oligomeric Bam HI-Xba I adaptor to generate the expression vector Zem219b (FIG. 13), into which mutant Bam HI-Xba I t-PA sequences were inserted.

Example 6—t-PA Analog Having a Substituted K1 Domain and Lacking a Growth Factor Domain A mutant sequence lacking the growth factor domain coding sequence is constructed by deletion mutagenesis using oligonucleotide ZC820 (5'GTA GCA CGT GGC CCT GGT TTT GAC AGG CAC TGA GTG3') and the single-stranded phage template M13-8100. A correct clone is identified by sequencing and designated "M13-8100-820." RF DNA of M13-8100-820 is digested with Bam HI and Xba I, and the doubly-mutagenized DNA fragment is isolated. Zem219b is digested with Bam HI and Xba I, and the large (vector) fragment is isolated and joined to the mutant fragment with T4 DNA ligase. After transformation, a correct clone is identified (8100-820) and transfected by electroporation into tk-BHK cells. The mutant protein is purified and characterized.

Example 7—t-PA Anlogs Having a Substituted K1 Domain and a Modified Growth Factor Domain

A. Replacement of Cys (83)

The t-PA coding sequence in Zem99 was mutagenized to encode a serine at position 83 (amino acid numbers refer to the sequence shown in FIG. 1). Zem99 was digested with Bam HI, and a 2.4 kb fragment comprising the t-PA coding sequence and the hGH terminator was isolated. This fragment was joined to Bam HI-digested M13mp18 (obtained from Pharmacia Japan Co.), and the resultant recombinant phage was used to transfect E. coli JM103. A phage clone having the desired insertion was designated "M13mp18/Bam-Zem99."

Figure 14:
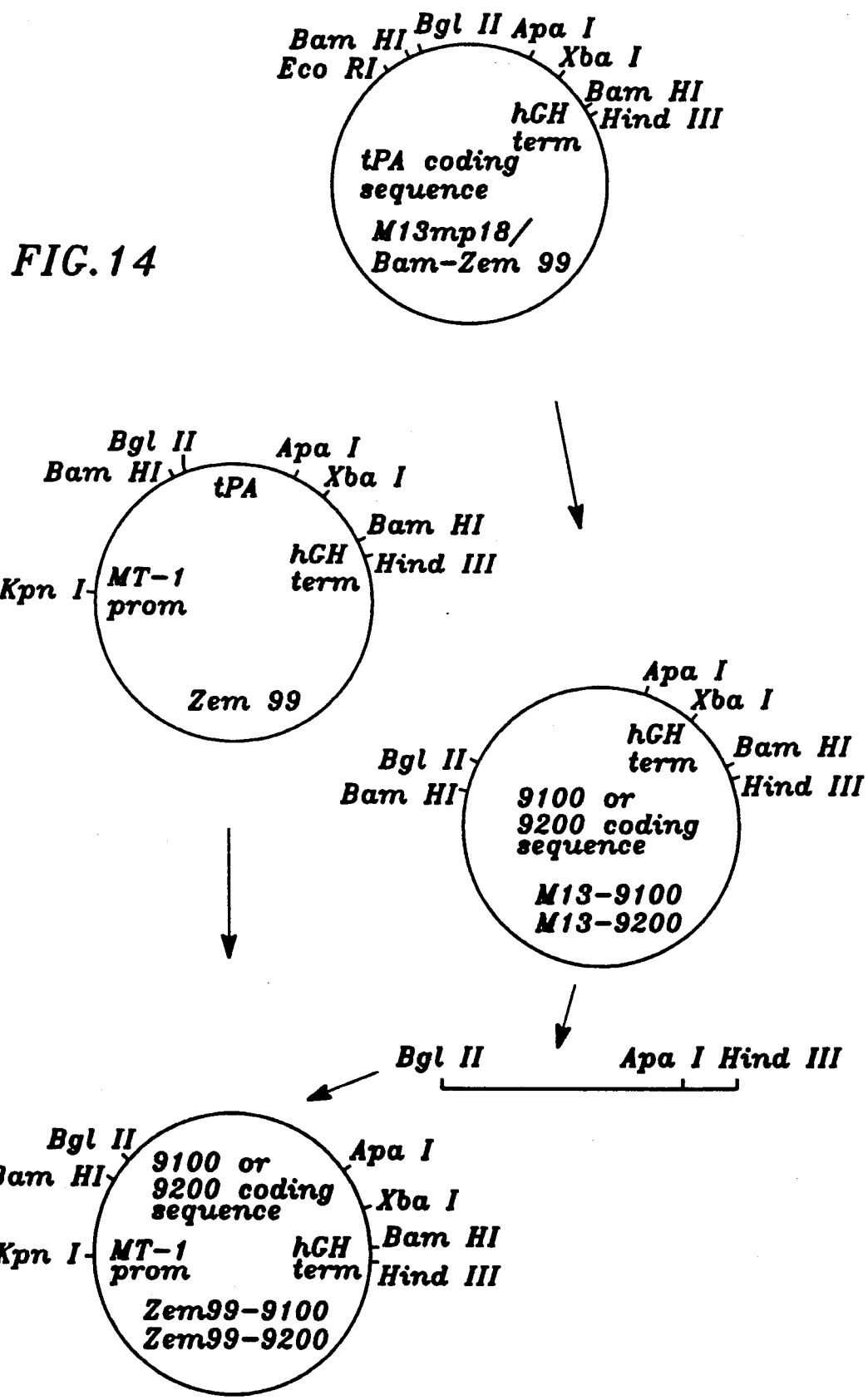
FIG. 14 illustrates the construction of plasmids Zem99-9100 and Zem99-9200.

For site-specific mutagenesis, an oligonucleotide (sequence 5'CT GGT ATC GAT TTC ACA GCT CTT CCC AGC A3') was synthesized and used as a mutagenic primer. The oligonucleotide was annealed to single-stranded M13mp18/Bam-Zem99. Mutagenesis was carried out according to standard procedures, and single-stranded DNA was isolated for sequencing. The replicative form of the mutagenized phage, designated "M13-9100RF," was digested with Bgl II and Hind III. A 2.3 kb fragment containing the t-PA sequence was recovered and joined to Zem99, which had been digested with Bgl II and Hind III (FIG. 14), and the DNA was used to transform E. coli TB1. A plasmid having the desired sequence alteration was recovered and designated "Zem99-9100" (FIG. 14). The mutated t-PA sequence of Zem99-9100 and the encoded amino acid sequence are shown in FIG. 15.

Plasmids Zem99-9100 and pSV2-dhfr were used to transfect tk-BHK cells by the method of Loyter et al. (ibid.). Transformants were subjected to cloning by the limiting dilution method. The mutant protein, designated "9100," was purified from the cell culture media by affinity purification.

An E. coli TB1 transformant containing plasmid Zem99-9100 has been deposited with the Fermentation Research Institute, Agency of Industrial Science and Technology, Ministry of International Trade and Industry, Japan (FRI), under Accession No. FERM BP-2820.

B. Replacement of Cys (84)

The t-PA DNA sequence was mutagenized to encode serine at amino acid 84 by means of site-specific mutagenesis using the oligonucleotide 5'CCT GGT ATC GAT TTC ACT GCA CTT CCC3'. The oligonucleotide was annealed to M13mp18/Bam-Zem99, and mutagenesis was carried out using standard procedures. Single-stranded mutagenized phage were sequenced, and a clone having the desired sequence alteration was selected. Replicative form DNA was prepared (designated "M13-9200RF") and digested with Bgl II and Hind III. The 2.3 kb t-PA fragment was isolated and joined to the Bgl II+Hind III-cut Zem99. The resultant vector was designated "Zem99-9200" (FIG. 14). The altered t-PA coding sequence of Zem99-9200 and the encoded amino acid sequence are shown in FIG. 16.

Zem99-9200 and pSV2-dhfr were used to co-transfect tk-BHK cells by the method of Loyter (ibid). Transformants were subjected to cloning by the limiting dilution method. The mutant protein (9200) was purified by affinity purification.

An *E. coli* RRl transformant containing plasmid Zem99-9200 has been deposited with FRI under Accession No. FERM BP-2161.

C. Combination of Cys Replacement and K1 Substitution

Single-stranded DNA was isolated from M13-9200 and was mutagenized using the oligonucleotide 5'GCA CGT GGC ACG CGT ATC TAT TTC3' to introduce an Mlu I site. The muagenized phage was designated "M13-92.05 PKA1." RF DNA was prepared from the mutant phage and was digested with Bgl II and Mlu I, and the 264 bp fragment was recovered. Zem99-8000 was digested with Mlu I and Apa I, and the 1126 bp fragment was recovered. These two fragments were joined to Bgl II, Apa I-digested Zem99, and the resultant plasmid was designated "Zem99-9280." This plasmid thus encodes a mutant t-PA with Ser at amino acid 84 and the K1 domain of plasminogen with Asp at position 96.

A second vector, which contains a mutant t-PA sequence encoding a t-PA analog with Ser at amino acid 84 and the K1 domain of plasminogen with Asn at position 96 was constructed. RF DNA from M13-92.05 PKA1 was digested with Bgl II and Mlu I, and the 264 bp fragment was recovered. Zem 99-8100 was digested with Mlu I and Apa I, and the 1126 bp fragment was recovered. These two fragments were joined to Bgl II, Apa I-digested Zem99, and the resultant plasmid was designated "Zem99-9281."

Example 8—Modification of Carbohydrate Attachment Sites in t-PA Analogs

An oligonucleotide primer (5'ACG GTA GGC TGT CCC ATT GCT AAA GTA GCA3') was prepared in order to replace Gly (183) and Ser (186) with Ser and Thr, respectively. Site-directed mutagenesis was performed according to standard procedures on the template M13mp18/Bam-Zem99 (Example 7). Single-stranded mutated phage DNA was prepared and sequenced. A clone having the desired sequence alteration was designated "M13-6000."

RF DNA of M13-6000 was isolated, digested with Bgl II and Apa I, and a fragment of approximately 1.4 kb was isolated. This fragment was joined to Bgl II, Apa I-digested Zem99 to produce the vector Zem99-6000. *E. coli* RRl transformed with Zem99-6000 has been deposited with the Fermentation Research Institute under Accession No. FERM P-9126.

Single-stranded M13-6000 DNA was mutagenized to introduce an Eco RV site into the mutant t-PA sequence. Mutagenesis was carried out by the one-primer method using the oligonucleotide 5'CTC AGA CGA TTC CAG GAT ATC GCA GAA CTC3'. The mutagenized phage was designated "M13-6000PKA2." RF DNA of M13-6000PKA2 was digested with Eco RV and Apa I, and the 890 bp fragment was recovered. Zem99-8000 was digested with Bgl II and Eco RV, and the 500 bp fragment was recovered. These two fragments were joined to Bgl II, Apa I-digested Zem99, and the resultant plasmid was designated "Zem99-8060."

Example 9: Characterization of Protein

Figure 17:
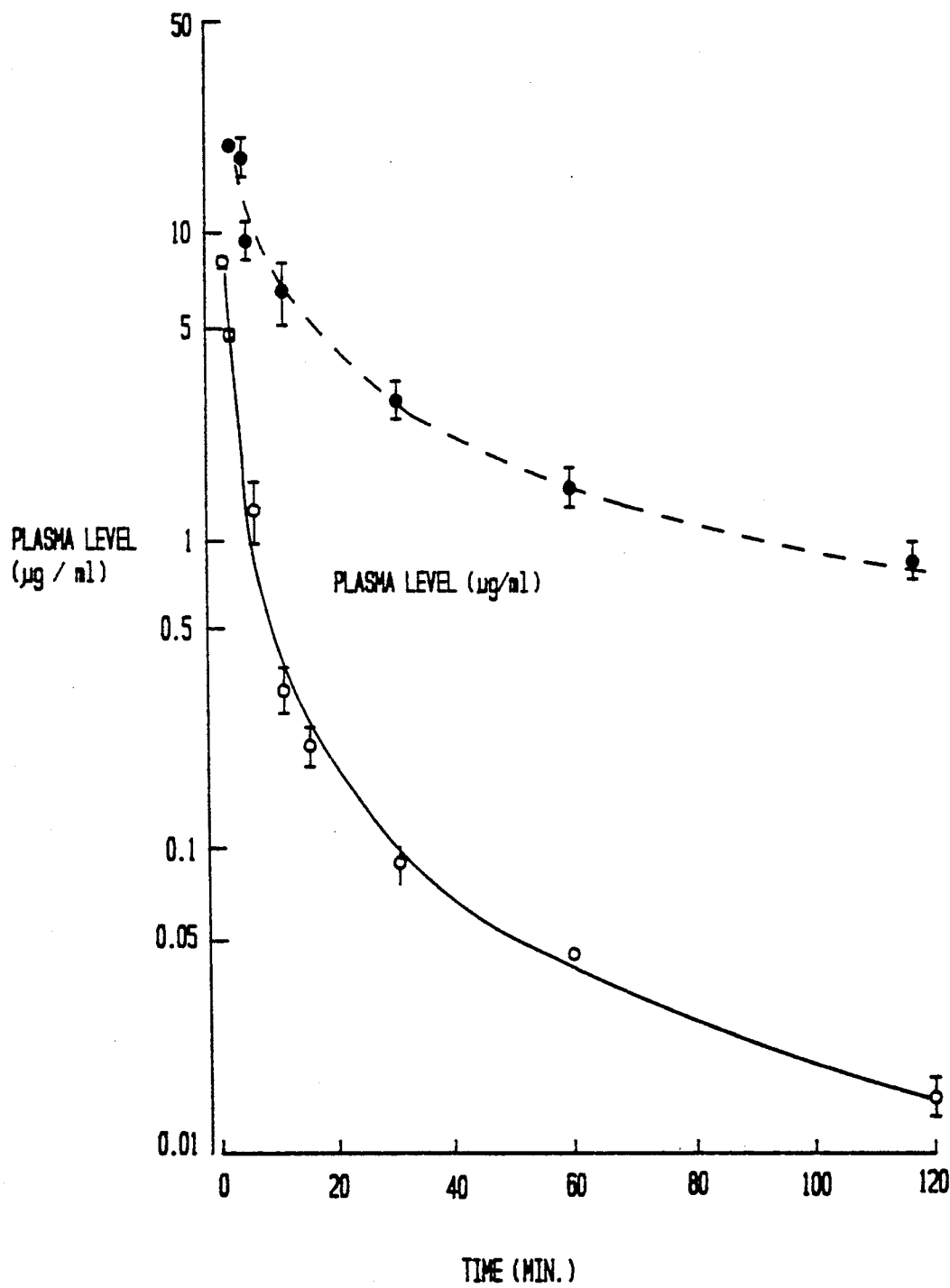
FIG. 17 shows a plot of plasma level vs. time for native t-PA and a representative t-PA analog which were administered to rats. (—) indicates native t-PA, (----) analog 8000.

Mutant protein #8000 was tested for plasma half-life, and the results were compared to a native t-PA (produced in recombinant BHK cells) control sample. Proteins to be tested were solubilized in a saline solution. The solutions were injected into the femoral veins of male Sprague-Dawley rats (230 g to 270 g each) at a dose of 0.4 mg/kg body weight. Blood samples (0.5 ml) were removed from the jugular veins, adjusted to 3.8% citric acid, centrifuged, and the plasma was removed. Plasma levels of t-PA protein were determined by a sandwich-type enzyme immunoassay. FIG. 17 shows a graph of blood level curves for native t-PA and protein #8000.

Changes in blood levels were analyzed by a two-compartment model (Shargel, L. and Yu, A.B.C., eds., *Applied Biopharmaceutics and Pharmacokinetics*, Appleton-Century-Crofts, N.Y., 1980, pp. 38–48). Half-lives were determined for the alpha and beta phases of clearance, and the back extrapolated intercept of the beta phase with the ordinate (B) and the area under the curve (AUC) were also determined. The values obtained for the various proteins are presented in Table 6.

TABLE 6

| Protein | T½(α) | T½(β) | B | AUC |
| --- | --- | --- | --- | --- |
| Native t-PA | 1.60 | 31.74 | 0.186 | 33.11 |
| 8000 | 2.66 | 31.06 | 5.908 | 340.39 | t-PA analog #8000 was tested for clot lysis activity using native recombinant t-PA as a control. A silk thread 3 cm in length was introduced into an Atom venous catheter (4Fr 3.5 cm) and the catheter was connected to an injection syringe. Human citrated blood was prepared by mixing blood and a solution of 3.8% sodium citrate in a 9:1 ratio. The citrated blood (0.5 ml) was combined with $^{125}$I-fibrinogen (25 μ Ci in 50 μl of physiological saline solution), 50 μl of 0.25M $CaCl_2$, and thrombn (5 U/10 μl of solution). Sixteen μl of the resulting solution was injected into the catheter, and the catheter was allowed to stand at room temperature for 60 minutes. The silk thread was then removed from the catheter and washed with a physiological saline solution. The radioactivity bound to the thread (the initial fibrin thrombus value) was determined. The thread was then introduced into a carotid arteriovein (A-V) shunt on a male Sprague-Dawley rat weighing between 200 and 300 grams. One ml samples of the protein in a saline solution containing 50 units heparin per ml were injected into the femoral vein of the animal. After two hours, the silk thread was removed from the shunt and the radioactivity (residual fibrin thrombus value) was determined. The residual thrombus ratio was determined according to the equation:

$$\text{Residual thrombus ratio} = \frac{\text{Residual fibrin thrombus value}}{\text{Initial fibrin thrombus value}} \times 100$$

Figure 18:
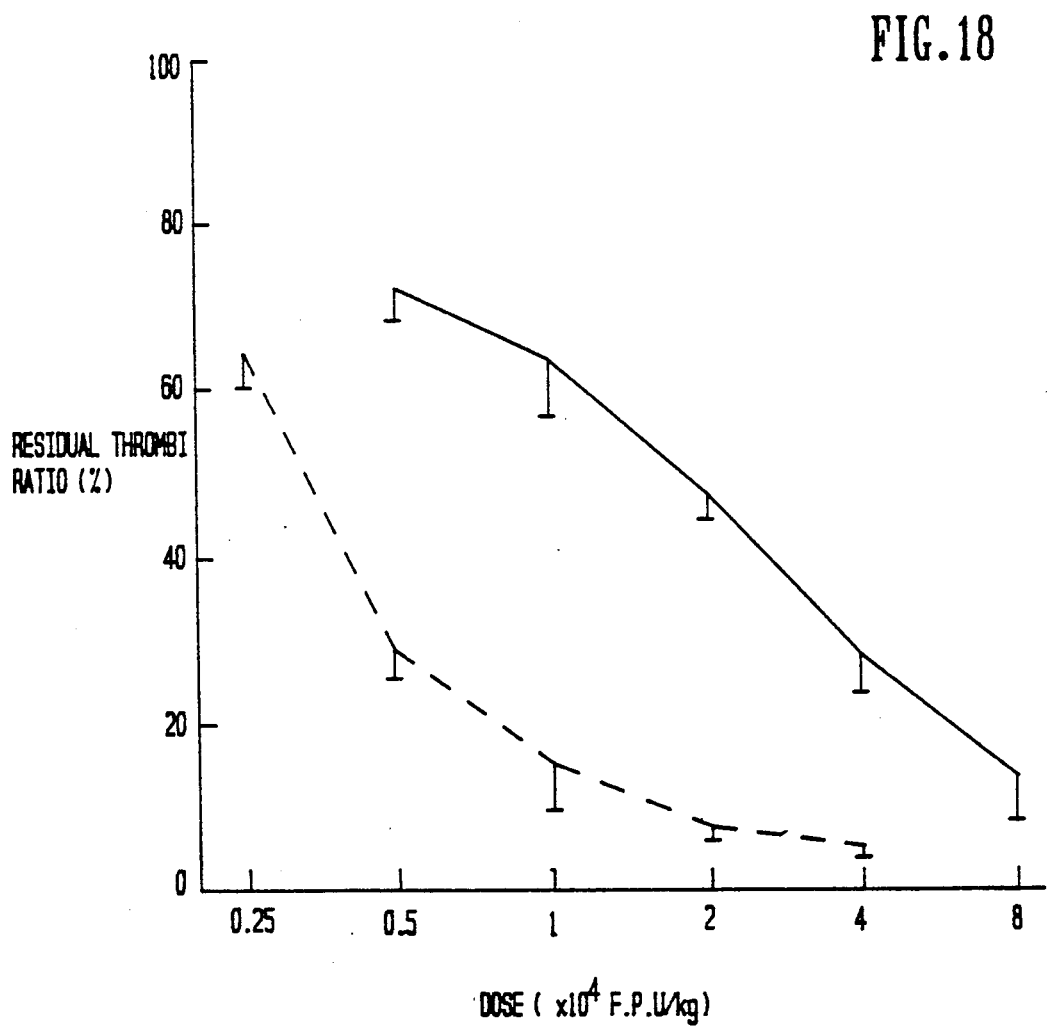
FIG. 18 shows the results of a clot lysis assay on native t-PA and a representative t-PA analog of the present invention. (—) indicates native t-PA, (----) analog #8000.

FIG. 18 is a graph of the results obtained using various doses of native t-PA and analog #8000. The data indicate that the mutant protein is superior to native t-PA in the ability to lyse clots in vivo.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A modified human t-PA wherein the K1 domain of native t-PA is replaced with another kringle domain selected from the group consisting of the human t-PA K2 domain, human plasminogen K1 domain, human plasminogen K4 domain, human plasminogen K5 domain, human factor XII kringle domain, human prothrombin K1 domain, and the human prothrombin K2 domain, said kringle domain mediating the binding of the modified human t-PA to fibrin, said kringle containing six cysteine residues, and said modified human t-PA exhibiting increased half-life or increased clot lysis activity as compared to native t-PA.

2. The modified t-PA of claim 1 wherein said kringle domain which replaces said K1 domain of native t-PA is composed of 78 to 82 amino acids.

3. The modified t-PA of claim 1 wherein said cysteine residues of the replaced kringle domain are located at
   (a) positions 1 and 22 relative to the N-terminus of the kringle domain, and
   (b) positions 1 and 6 relative to the C-terminus of the kringle domain, and
   (c) one position selected from the group consisting of positions 18 and 19 relative to the C-terminus of the kringle domain, and
   (d) one position selected from the group consisting of positions 29, 30 and 31 relative to the C-terminus of the kringle domain as shown in FIG. 20.

4. The modified t-PA of claim 1 wherein said kringle domain comprises the amino acid sequence:
Cys Lys Thr Gly X Gly Lys Asn Tyr Arg Gly Thr Met Ser Lys Thr Lys Asn Gly Ile Thr Cys Gln Lys Trp Ser Ser Thr Ser Pro His Arg Pro Arg Phe Ser Pro Ala Thr His Pro Ser Glu Gly Leu Glu Glu Asn Tyr Cys Arg Asn Pro Asp Asn Asp Pro Gln Gly Pro Trp Cys Tyr Thr Thr Asp Pro Glu Lys Arg Tyr Asp Tyr Cys Asp Ile Leu Glu Cys
wherein X is Asp or Asn.

5. A DNA sequence, encoding a modified human t-PA wherein the K1 domain of native t-PA is replaced with another kringle domain selected from the group consisting of the human t-PA K2 domain, human plasminogen K1 domain, human plasminogen K4 domain, human plasminogen K5 domain, human factor XII kringle domain, human prothrombin K1 domain, and the human prothrombin K2 domain, said kringle domain mediating the binding of the modified human t-PA to fibrin, said kringle containing six cysteine residues, and said modified human t-PA exhibiting increased half-life or increased clot lysis activity as compared to native t-PA.

6. An expression vector containing a DNA sequence encoding a modified human t-PA wherein the K1 domain of native t-PA is replaced with another kringle domain selected from the group consisting of the human t-PA K2 domain, human plasminogen K1 domain, human plasminogen K4 domain, human plasminogen K5 domain, human factor XII kringle domain, human prothrombin K1 domain, and the human prothrombin K2 domain, said kringle domain mediating the binding of the modified human t-PA to fibrin, said kringle containing six cysteine residues, and said modified human t-PA exhibiting increased half-life or increased clot lysis activity as compared to native t-PA.

7. The expression vector of claim 6 wherein said vector is Zem99-8000 or Zem99-8100.

8. A host cell transfected or transformed with an expression vector containing a DNA sequence encoding a modified human t-PA wherein the K1 domain of native t-PA is replaced with another kringle domain selected from the group consisting of the human t-PA K2 domain, human plasminogen K1 domain, human plasminogen K4 domain, human plasminogen K5 domain, human factor XII kringle domain, human prothrombin K1 domain, and the human prothrombin K2 domain, said kringle domain mediating the binding of the modified human t-PA to fibrin, said kringle containing six cysteine residues, and said modified human t-PA exhibiting increased half-life or increased clot lysis activity as compared to native t-PA.

9. The host cell of claim 8 wherein said expression vector is Zem99-8000 or Zem99-8100.

10. The host cell of claim 8 wherein said host cell is *E. coli* or a mammalian host cell.

11. The host cell of claim 8 wherein said host cell is a BHK cell.

12. A pharmaceutical composition comprising a modified human t-PA wherein the K1 domain of native t-PA is replaced with another kringle domain selected from the group consisting of the human t-PA K2 domain, human plasminogen K1 domain, human plasminogen K4 domain, human plasminogen K5 domain, human factor XII kringle domain, human prothrombin K1 domain, and the human prothrombin K2 domain, said kringle domain mediating the binding of the modified human t-PA to fibrin, said kringle containing six cysteine residues, and said modified human t-PA exhibiting increased half-life or increased clot lysis activity as compared to native t-PA, and a physiologically acceptable carrier or diluent.

* * * * *

UNITED STATES PATENT AND TRADEMARK OFFICE
CERTIFICATE OF CORRECTION

PATENT NO.    : 5,149,533
DATED         : September 22, 1992
INVENTOR(S)   : Mulvihill et al.

It is certified that error appears in the above identified patent and that said Letters Patent is hereby corrected as shown below:

In column 25, claim 5, line 35, after "sequence" and before "encoding", please delete ",".

Signed and Sealed this

Ninth Day of January, 1996

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.   :   5,149,533
DATED        :   September 22, 1992
INVENTOR(S)  :   Eileen R. Mulvihill et al.

It is certified that error appears in the above-indentified patent and that said Letters Patent is hereby corrected as shown below:

Title page, item [75] inventors, please delete

"Bjorn A. Nexo, Soborg, Denmark".

Signed and Sealed this

Eighteenth Day of February, 1997

Attest:

BRUCE LEHMAN

*Attesting Officer*    *Commissioner of Patents and Trademarks*